United States Patent
Porter

(10) Patent No.: US 8,927,299 B2
(45) Date of Patent: Jan. 6, 2015

(54) SAMPLE CARRIER FOR EFFECTING CHEMICAL ASSAYS

(75) Inventor: Robert Andrew Porter, Wymington (GB)

(73) Assignee: The Secretary of State for Innovation, Universities and Skills of Her Majesty's Britannic Government, London (GB)

( * ) Notice: Subject to any disclaimer, the term of this patent is extended or adjusted under 35 U.S.C. 154(b) by 989 days.

(21) Appl. No.: 13/002,644

(22) PCT Filed: May 26, 2009

(86) PCT No.: PCT/GB2009/001315
§ 371 (c)(1),
(2), (4) Date: Sep. 23, 2011

(87) PCT Pub. No.: WO2010/004244
PCT Pub. Date: Jan. 14, 2010

(65) Prior Publication Data
US 2012/0034708 A1 Feb. 9, 2012

(30) Foreign Application Priority Data

Jul. 10, 2008 (GB) .................................... 0812679.9

(51) Int. Cl.
*G01N 33/536* (2006.01)
*G01N 33/543* (2006.01)

(52) U.S. Cl.
CPC .............................. *G01N 33/54366* (2013.01)
USPC ........... 436/536; 436/501; 436/518; 436/526; 436/538; 436/164; 436/166; 436/172; 435/283.1; 435/288.3; 435/288.4; 435/288.5

(58) Field of Classification Search
USPC ......... 436/501, 518, 526, 536, 538, 164, 166, 436/172; 435/283.1, 288.3, 288.4, 288.5
See application file for complete search history.

(56) References Cited

U.S. PATENT DOCUMENTS 5,835,329 A 11/1998 Sucholeiki
5,863,502 A 1/1999 Southgate et al.
(Continued)

FOREIGN PATENT DOCUMENTS

CN 101175997 A 5/2008
EP 1611836 1/2006
(Continued)

OTHER PUBLICATIONS

Wang et al., "Spectroscopic studies of thiocyanate in silver hydrosol and the influence of halide ions," Spectrochimica Acta Part A, vol. 55, pp. 991-998 (1999).
(Continued)

*Primary Examiner* — Melanie Y Brown
(74) *Attorney, Agent, or Firm* — Edward J. Baba; Daniel Stoddard; Bozicevic, Field & Francis LLP

(57) ABSTRACT

There is disclosed apparatus and a system for effecting testing on a sample, such as for medical testing. The apparatus includes a sample chip (30) provided with at least two chambers (48, 50) within which analyte and a sample to be tested can be located, one chamber being a mixing chamber (48) and the other a detection chamber (50), the latter being provided with a sensor or means to enable sensing of one or more parameters pertaining to the sample. A detector unit (70, 170) includes a slot (76) for holding a sample carrier (30), drive means (94) for moving parts of a sample from the mixing chamber (48) to the detection chamber (50), such as by electromagnetic force, sensing means (60) for sensing the one or more parameters, a diagnostic unit (84) for analyzing the sensed parameters and a display unit (72) for displaying the results of the test to a user. The test unit (70, 170) is preferably handheld, which the sample carrier (30) is preferably in the form of a disposable chip.

27 Claims, 23 Drawing Sheets

(56) References Cited

U.S. PATENT DOCUMENTS

| | | | |
|---|---|---|---|
| 6,159,739 A * | 12/2000 | Weigl et al. ............... 436/52 |
| 6,159,747 A * | 12/2000 | Harttig et al. ............. 436/518 |
| 6,300,141 B1 | 10/2001 | Segal et al. |
| 6,319,469 B1 | 11/2001 | Mian et al. |
| 6,326,612 B1 * | 12/2001 | Elkind et al. ............... 250/239 |
| 6,975,395 B1 | 12/2005 | Gentieu et al. |
| 7,045,364 B2 | 5/2006 | Limoges et al. |
| 7,226,562 B2 | 6/2007 | Holl et al. |
| 7,745,228 B2 * | 6/2010 | Schwind et al. ............ 436/164 |
| 8,445,293 B2 * | 5/2013 | Babu et al. ............... 436/514 |
| 8,507,260 B2 * | 8/2013 | Alajem et al. ............ 435/287.7 |
| 2001/0035955 A1 | 11/2001 | Ruevski et al. |
| 2002/0137218 A1 | 9/2002 | Mian et al. |
| 2002/0197733 A1 * | 12/2002 | Bohm et al. ............... 436/180 |
| 2003/0186274 A1 | 10/2003 | Limoges et al. |
| 2004/0028566 A1 * | 2/2004 | Ko et al. ............... 422/100 |
| 2004/0058457 A1 | 3/2004 | Huang et al. |
| 2004/0248093 A1 | 12/2004 | Coombs et al. |
| 2005/0230713 A1 | 10/2005 | Brousseau, III |
| 2006/0228814 A1 | 10/2006 | Limoges et al. |
| 2006/0263818 A1 | 11/2006 | Scherer et al. |
| 2006/0270049 A1 | 11/2006 | Todd |
| 2007/0148039 A1 | 6/2007 | Padmanabhan et al. |
| 2007/0202561 A1 * | 8/2007 | Rosenstein ............... 435/14 |
| 2010/0034742 A1 | 2/2010 | Schwartz et al. |
| 2011/0124008 A1 | 5/2011 | Nam et al. |

FOREIGN PATENT DOCUMENTS

| | | |
|---|---|---|
| JP | 2001521171 | 5/1999 |
| JP | 2003502670 | 1/2003 |
| JP | 2004-279179 A | 10/2004 |
| JP | 2007514142 | 5/2007 |
| JP | 2007-530413 A | 11/2007 |
| WO | 9002938 | 3/1990 |
| WO | 9828623 | 7/1998 |
| WO | 9853301 | 11/1998 |
| WO | 9938612 | 8/1999 |
| WO | 0013014 | 3/2000 |
| WO | 0025136 | 5/2000 |
| WO | 0167079 | 9/2001 |
| WO | 2004016160 | 2/2004 |
| WO | 2004020112 | 3/2004 |
| WO | 2004113919 | 12/2004 |
| WO | 2005046437 | 5/2005 |
| WO | 2005121792 | 12/2005 |
| WO | 2006065762 | 6/2006 |
| WO | 2006118420 | 11/2006 |
| WO | 2007/110779 | 10/2007 |
| WO | 2008002462 | 1/2008 |
| WO | 2008010058 | 1/2008 |
| WO | 2008074146 | 6/2008 |

OTHER PUBLICATIONS

Yang et al., "Determination of trace thiocyanate with nano-silver coated multi-walled carbon nanotubes modified glassy carbon electrode," Analytica Chimica Acta, vol. 585, pp. 331-336 (2007).

Kim, et al. (2006) "Superparamagnetic Nanoparticle-Based Nanobiomolecular Detection in a Microfluidic Channel" Current Applied Physics 6(6):976-981.

Dequaire et al., "An Electrochemical Metalloimmunoassay Based on a Colloidal Gold Label" Anal. Chem. 72:5521-5528 (2000).

Fritzsche and Taton, "Metal nanoparticles as labels for heterogeneous, chip-based DNA detection," Nanotechnology 14, R63-R73 (2003).

Guo and Wang, "Synthesis and electrochemical applications of gold nanoparticles," Analytica Chimica Acta 598, 181-92 (2007).

* cited by examiner

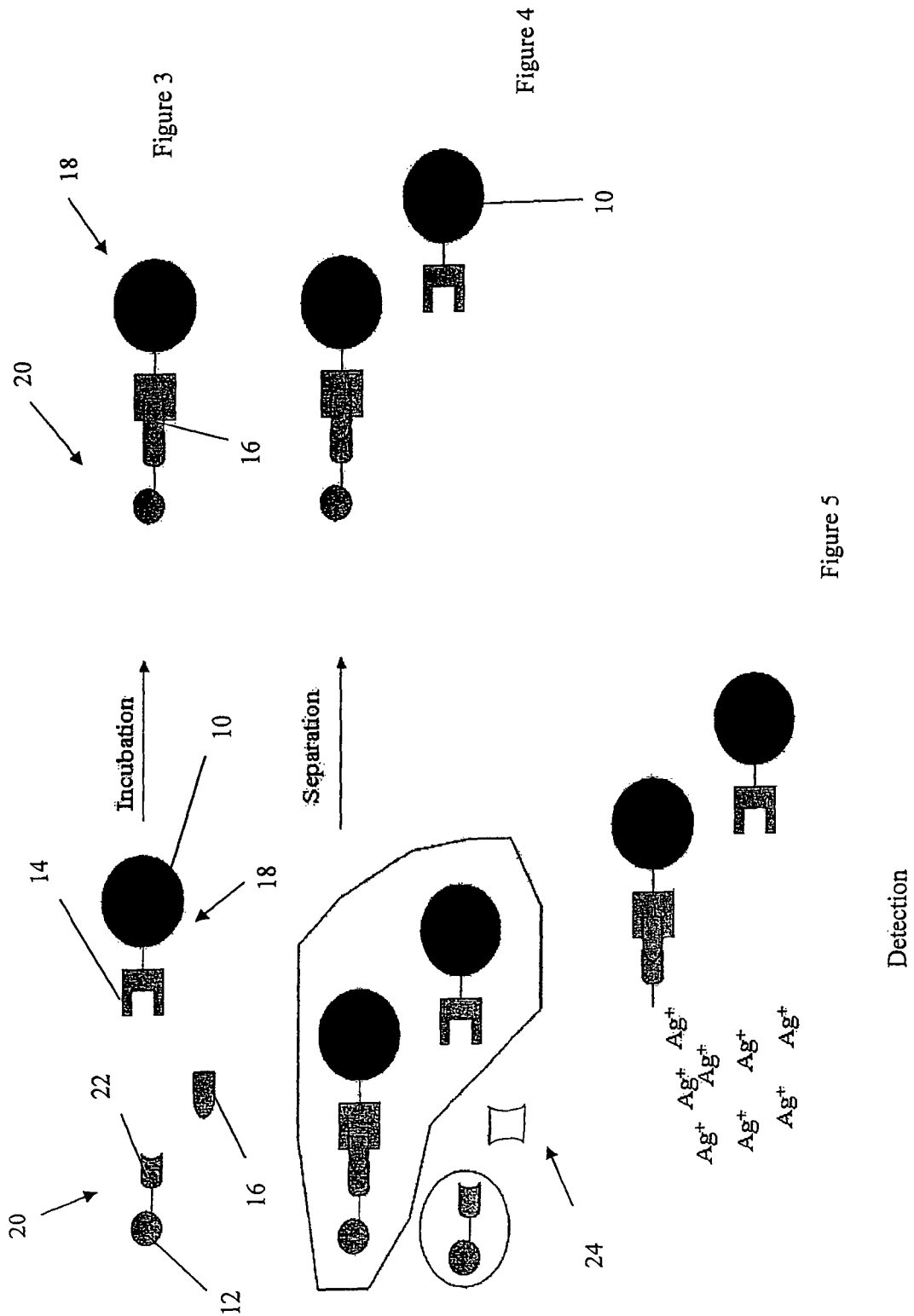

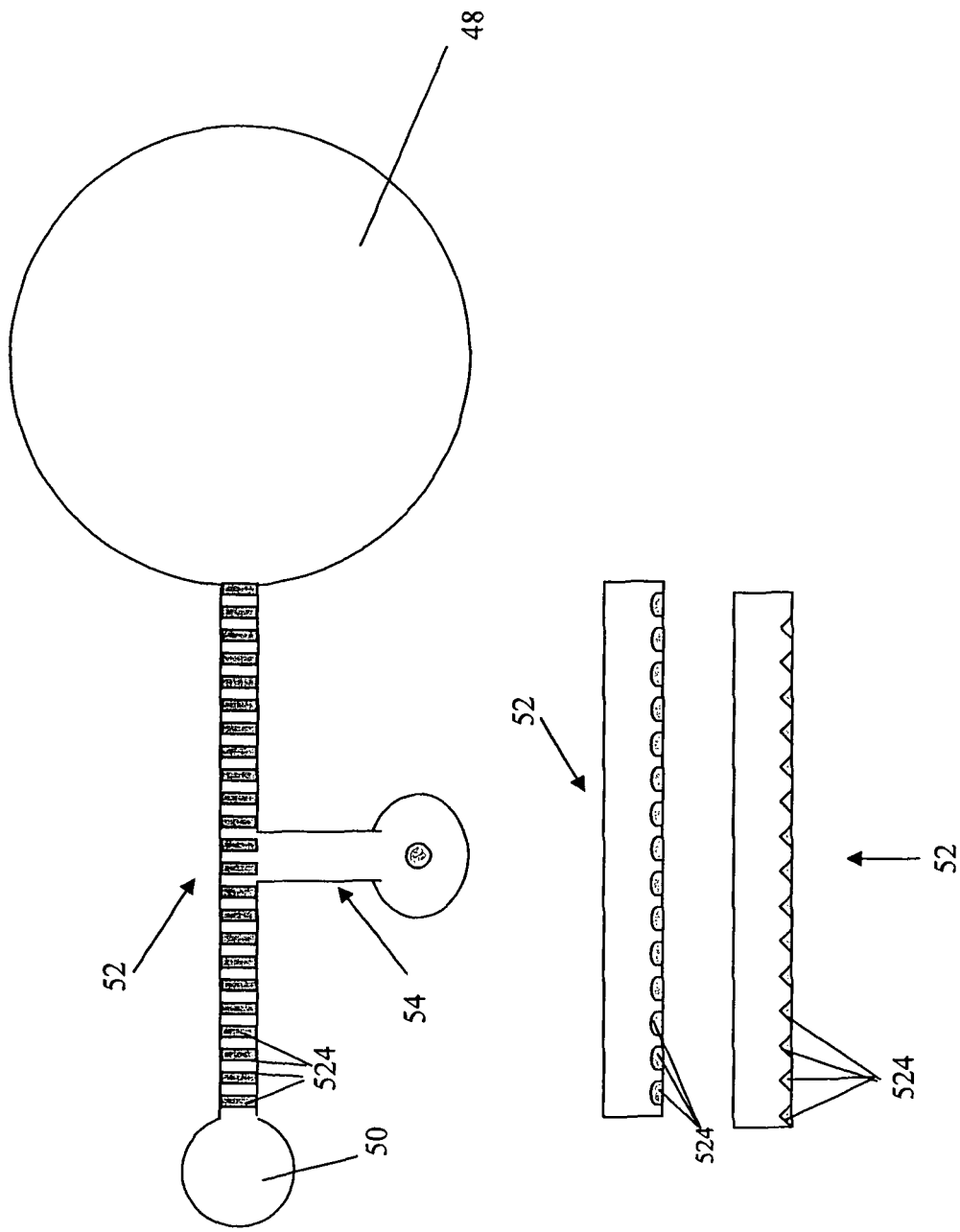

SAMPLE CARRIER FOR EFFECTING CHEMICAL ASSAYS

The present invention relates to a sample carrier for effecting chemical testing and in the preferred embodiments for conducting an electrochemical assay utilising metal nanoparticles as an electrochemical label.

Much work has been done towards the provision of a portable device for "point-of-care" medical testing. The majority of this work has been directed towards the development of a so-called "laboratory-on-a-chip". The purpose of such devices is to take a biological sample and then proceed to test it for the presence of various antigens.

US-2006/0263818 discloses a system in which antigens, a sample and labelled polyclonal antibodies are successively flowed in a grid, the antigens and antibodies flowing in one direction, and the sample flowing perpendicularly to this. At each of the crossing points of the samples and antigens/antibodies, an indicative number of labelled antibodies amassed. The labels on these antibodies may be a fluorophore that generates a light signal, from which conventional fluoroscopic detection techniques can quantify the antigen. By providing a grid of 5×10 paths, the device is able simultaneously to run five tests on ten samples.

Prior art devices seeking to provide a "laboratory on a chip" aim to be complete integral units which carry out specific chemical or biochemical assays and which generate and display the analysis results of the assays, all in a manner which is self-contained and substantially foolproof. There is thus no need with these devices to have any other equipment and little control by the user.

However, devices of this nature can be expensive to produce and their performance is often dictated by their size, nature and cost pressures. In addition, in order to make such devices more generally useful, they tend to provide for the testing of a variety of conditions. One device, for example, exposes a specimen to five tests, of which one or more may be unnecessary. Furthermore, these devices are not readily adaptable to different tests. For example, if a new antigen is discovered it is necessary to provide a new device specifically designed and prepared for testing this.

U.S. Pat. No. 6,319,469 discloses methods and apparatus for performing microanalytic and microsynthetic analysis and procedures. It provides a disk with radial components which can be spun so that centripetal forces cause fluids on the disk surface to move.

WO 2004/113919 discloses methods and devices for detecting the presence of a particle of interest. In one embodiment, a sample is introduced and forced through a filter to a collecting chamber, from where it is forced back through the filter by the introduction of a reagent in the opposite direction. The filter retains for analysis only reacted antigens since the unreacted particles are smaller (not having acquired a labelling antibody) and can pass through. Another embodiment discloses the introduction of the sample into a mixing channel into which is also added the reagent. The reagent mixes with the sample in the mixing channel and they pass into a detection chamber bordered by a filter. Again, the smaller unreacted particles pass through the filter, leaving the reacted antigens to be detected.

U.S. Pat. No. 7,226,562 discloses a device in which reagent is mixed with sample on the way to an analysis region.

However in these devices unreacted reagent passes into the detection zone and without some means to remove the unreacted reagent from the detection zone, it remains there. When performing assays, unreacted reagent in the detection zone can trigger false readings which can invalidate the result.

The present invention seeks to provide improved apparatus and methods for effecting chemical and biochemical analysis.

According to an aspect of the present invention, there is provided a sample carrier for use in testing for the presence of a substance in a sample, including: a sample support element, a mixing zone and a detection zone within or on the sample support element, a coupling channel between the mixing and detection zones operable to provide for the transfer of the sample to be tested into the mixing zone, and for the transfer of reagents between the mixing and detection zones, and an inlet for the sample to be tested within or on the sample support element coupled to the channel between the mixing and detection zones.

The sample carrier provides a simple and effective structure by which one or more analyses can be carried out on a sample. In the preferred embodiment, the sample carrier provides for rapid testing of one or at most a few elements of a sample, allowing fast testing and analysis.

Substance entering the mixing zone is therefore moving away from the detection, zone and does not force unreacted reagent into the detection zone. Unreacted sample in the detection zone is not as problematic as unreacted reagent since unreacted sample will not trigger readings.

Preferably, the inlet is coupled to the channel between the mixing and detection zones such that flow of sample fluid into the device pushes apart elements in the mixing and detection zones. This can further ensure that false readings are not generated by specifically pushing unreacted reagent away from the detection zone.

Advantageously, the channel provides for movement of liquids therethrough by capillary action. By this feature, the sample carrier can provide a self-contained sample collection and holding device.

Advantageously, the carrier is formed as a substantially planar structure.

In an embodiment, the sample support element forms a wall of a casing. This is the preferred embodiment as the sample can be housed securely within a casing for test and disposal purposes, particularly useful when testing for contagious substances.

Advantageously, the casing is formed as a sandwich structure including first and second cover layers and at least one intermediate layer having recesses or apertures therein for providing the chambers and conduit, one of the first and second cover layers providing the inlet port to the conduit.

This is a simple structure which can be manufactured easily and cheaply. It is envisaged that the intermediate layer could be a film, of plastics or other suitable material, or even printed on one of the outer layers, for example by inkjet printing.

In another embodiment, recesses to form the chambers and channels are etched into one of the outer layers.

Another embodiment provides a sample carrier in which the sample support element includes a plurality of hydrophilic regions providing the mixing and detection zones, the conduit and inlet.

Yet another embodiment provides a sample support element which includes recessing providing the mixing and detection zones, the conduit and inlet.

Preferably, the sample carrier includes at least one detector terminal arranged in communication with the detection zone.

At least one detector terminal may include an electrical terminal; or it may include an optical terminal, a resonance terminal, a plasmodic terminal, a vibrational terminal or an acoustic wave terminal.

In a preferred embodiment, the sample carrier includes an identifier element, preferably operable to identify a category of the carrier and most preferably including a coding unit.

The identifier element may include a memory element operable to provide data related to the test associated with the sample carrier. It may also include data transferable to a tester unit associated with the sample carrier.

In the preferred embodiment, the mixing chamber is loaded with a fluid provided with carrier elements and label elements and/or the detection chamber is loaded with a label detecting element.

In an embodiment, the label detecting element is operable to ionise the label elements and to generate therefrom ions measurable by electrical detection.

The disclosure herein also contemplates a test device for testing for one or more characteristics of a sample carried by a sample carrier, including a control unit; a movement unit operable to effect movement of a sample to be tested within the sample carrier; a sensing unit operable to sense one or more parameters relating to the contents or characteristics of the sample; diagnostic means operable to determine a diagnostic condition on the basis of the sensed parameter or parameters and an information unit operable to provide information relating to the diagnosis.

The disclosure also contemplates a test device for testing for one or more characteristics of a sample carried by a sample carrier, which test device is in the form of an attachment device attachable to a portable electronic processing device; the attachment device including a movement unit operable to effect movement of a sample to be tested within the sample carrier; a sensing unit operable to sense one or more parameters relating to the contents or characteristics of the sample; and an interface unit to a control unit of an electronic processing device for use in determining a diagnostic condition on the basis of the sensed parameter or parameters and for providing information relating to the diagnosis.

Embodiments of the present invention are described below, by way of example only, with reference to the accompanying drawings, in which:

FIG. 3 is a schematic diagram of the first stage of the analysis procedure, termed an incubation stage;

FIG. 4 is a schematic diagram of a separation stage of the analysis procedure;

FIG. 5 shows a stage of the analysis procedure after dissolution of the silver sol particles;

FIG. 44 is a schematic diagram of an embodiment of testing chambers for a test chip or strip with bumps in the conduit;

FIG. 45 is a side sectional view of the conduit of FIG. 44;

FIG. 46 is a side sectional view of another embodiment of testing chambers for a test chip or strip with bumps in the conduit.

It is to be understood that the Figures are provided for illustration purposes only and are not to scale. In many instances, the drawings show elements much larger that they would be in practice, as the skilled person will readily appreciate.

FIGS. 1 to 5 and the accompanying description below provide an example of a chemical analysis method suitable for being performed in the apparatus devices disclosed herein. Further details of this chemical assay are disclosed in the applicant's co-pending British patent application number 0723137.6.

The illustrated chemical analysis steps are just one of a variety of examples for which the apparatus disclosed herein could be adapted to work.

Figure 1:
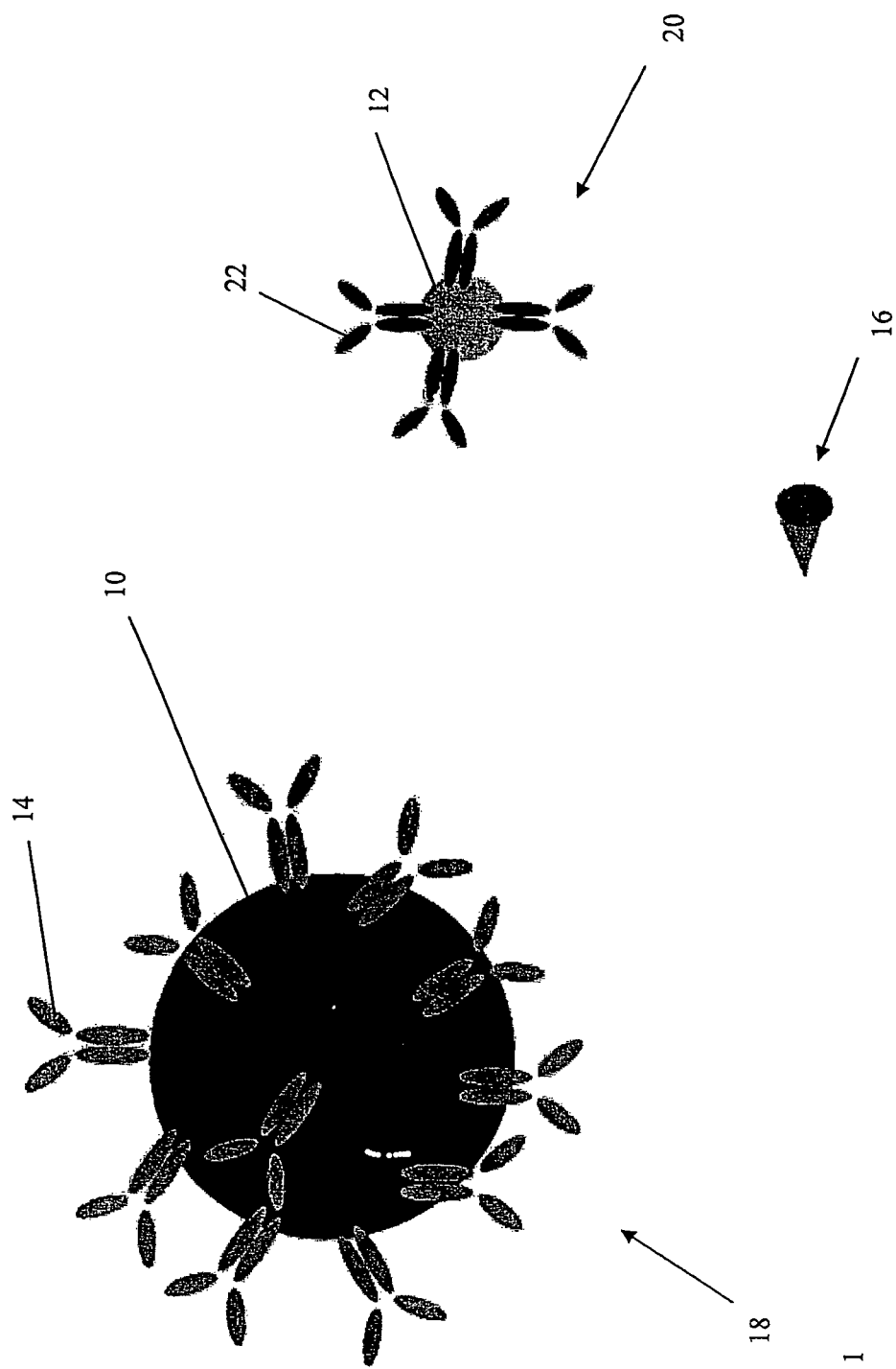
FIG. 1 is a schematic diagram of the various elements used in an embodiment of test method, including a magnetic particle to which antibodies are attached, a silver sol particle to which one or more antibodies are attached and an antigen.
Figure 2:
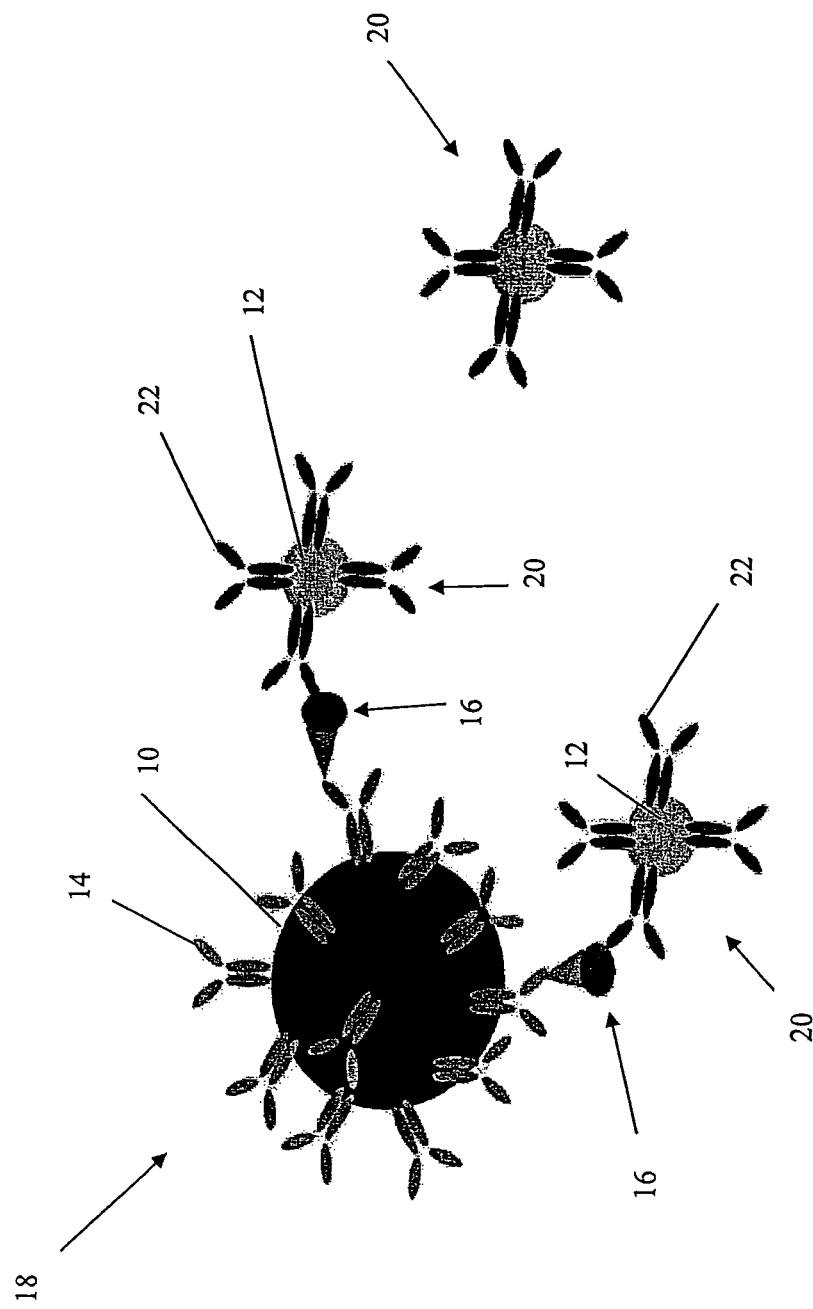
FIG. 2 is a schematic diagram showing the elements of FIG. 1 bound together in a first stage of the analysis procedure.

As shown in FIGS. 1 and 2, the method shown utilises a magnetic particle 10, preferably a super paramagnetic particle such as an arsenic solid phase, and a metal label, typically a particulate label which is preferably a silver sol 12. Silver is preferable as it forms stable sols which can easily be oxidised to form silver ions. The magnetic particle 10 is attached to a first binding moiety, preferably one or more antibodies 14, which is capable of binding to an analyte of interest. The analyte of interest is preferably an antigen 16 but can also be an antibody, a mimotype or nucleic acid strand. The magnetic particle 10 with its attached antibodies 14 forms a magnetic support 18.

The silver sol particle 12 is attached to a second binding moiety to form a metal label 20. The second binding moiety, preferably one or more antibodies 22, is capable of binding to a different region of the antigen 16.

In practice, a plurality of magnetic particles 10 and labels 12 is provided in solution or suspension, for reaction with a plurality of antigens 16 in a sample to be tested.

Referring next to FIG. 2, the elements of FIG. 1 are shown once they have become bound to one another, typically after an incubation period in a suitable reaction chamber, examples of which are described below. An antibody 14 of the magnetic particle 10 and an antibody 22 of the particulate label 12 bind to an antigen 16, in effect sandwiching the antigen 16 between them. A plurality of antigens 16 can be bound to each magnetic particle 10. The composition is such that only the right antigen 16, that is the antigen sought to be detected and measured, can bind to the antibodies 14 and 22 of the magnetic particle 10 and label 12. Any other antigens or other substances in the mix will not bind to the magnetic particle 10 and neither to the label 12.

The combination is such that the antigens 16 become attached to a carrier device, the magnetic particle, as well as to a label, in this example the silver sol particle 12. The antigens can thus be made to move and then to be detected, in particular by using the silver of the label 12, as described below.

Referring now to FIGS. 3 to 5, these depict in graphical form the binding of the various elements together, the separation of the magnetic particles from the remainder of the solution or suspension and the detection of the labels carried by the antigens. For ease of description, the three stages shown are depicted as the incubation stage, the separation stage and the detection stage. The term incubation is not intended to imply any particular process apart from allowing the sample to mix with the carrier and label particles and to allow the element to be tested to be attached to these.

FIG. 3 depicts the incubation stage, in which in a suitable mixing chamber and held in a suitable inert carrier fluid there are provided a plurality of magnetic particles 10, a plurality of labels 12 and then a specimen to be tested. In this example, the specimen includes a plurality of antigen particles 16. The antigen particle 16 is depicted as being of a particular type, shown as a particular shape in the drawing. The antibodies 14 and 22 of the particles 10 and 12 respectively are compatible only with that antigen 16 and are depicted as having complementary shapes. In this schematic representation, the magnetic particle 10 is shown having a single antibody particle 14 but in practice will be provided with a plurality of these.

Thus during this first phase the antigen 16 binds to the antibodies 14 and 22 to form the complex shown at the right hand side of the Figure. Any other antigens in the specimen will not bind either to the magnetic particle 10 or the label 12 and thus will remain isolated in suspension. These antigens could be said, following the representation in FIG. 3, to have a different shape with which the antibodies 14 and 22 are not compatible.

FIG. 4 shows the second phase in the procedure, that is the separation phase. The magnetic properties of the particles 10 are used to move these outside the mixing chamber to a second, detection chamber. Typically, this is achieved by the generation of a magnetic or electromagnetic force used to push or drag the magnetic particles 10 in the desired direction. Apparatus and methods for achieving this are described in detail below.

During separation, therefore, all or substantially all of the magnetic particles 10 are removed from the mixing chamber, including those to which no antigen 16 has bound. What is left in the mixing chamber is any antigens 24 incompatible with the antibodies 14, 22, that is not desired to be analysed, and labels 12 which have not bound to a magnetic particle 10 through an appropriate antigen 16.

Referring now to FIG. 5, there is shown the final phase of the process, that is the detection phase. Once the magnetic particles 10 have reached the detection chamber, the silver sol is oxidised. This in effect dissolves the silver of the label and produces silver ions which dissolve into the carrier fluid. It will be appreciated that since only the correct antigens 16 will have been transported by the magnetic particle 10 and since only these will carry with them a label 12, the amount of silver ions produced by oxidation will be directly related to the number/amount of the antigens sought to be detected in the original specimen. Any magnetic particles 10 which are transported to the detection chamber but which do not carry any antigen 16 will not carry a label 12 either and thus will not affect amount of silver ion generated by oxidation.

In one embodiment, the detection chamber is provided with ammonium thiocyanate which removes the silver sol from its biocomplex and forms a monolayer chemically bound around the silver sol resulting in a negatively charged nanoparticle. This charged nanoparticle can be migrated under an electrical potential to a positively charged electrode. The silver sol at that electrode is then dissolved under an oxidative potential to form silver ions $Ag^+$, which can then be measured by accumulation stripping voltammetry (ASV). ASV is an analytical technique that involves preconcentration of a metal phase onto an electrode surface and selective oxidization of each metal phase species during an anodic potential sweep.

A small proportion of the silver ions measured may be in the form of a complex with a chelating agent where the release agent is capable of chelating the silver ions.

The use of silver sol as a label 12 gives a molecular amplification of the electrochemical signal, as each 40 nm silver sol particle contains approximately $10^6$ silver ions. Thus the sensitivity of the assay is enhanced and only a small amount of sample is required. Furthermore, silver forms stable sols for use as a biolabel. It also easily oxidized to form silver ions.

FIGS. 1 to 5 and the above description relate to just one example of a suitable collection and detection procedure using a particular antibody/antigen mechanism, transport and labelling arrangement and oxidation method. However, the apparatus and methods described below are not limited to the application of this method alone and could be used with other detection mechanisms, that is with different analyte capturing and detecting mechanisms, as well as with other label detection methods.

Figure 6:
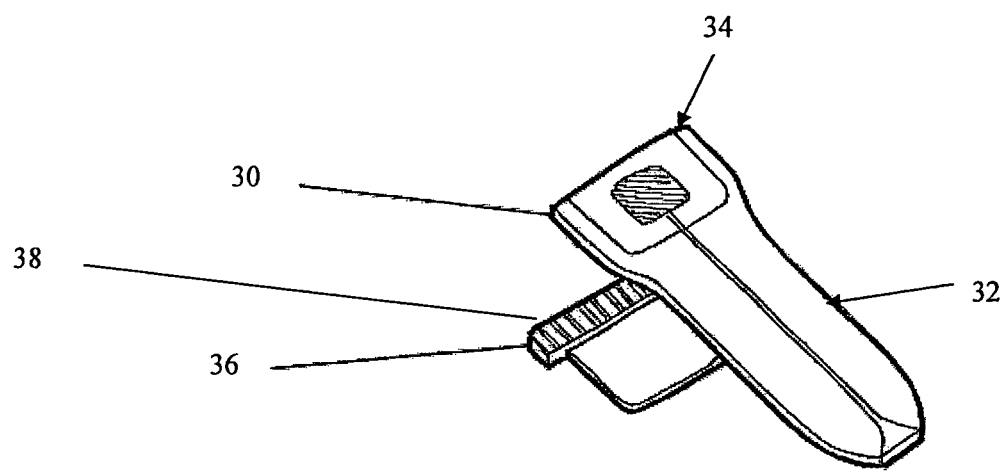
FIG. 6 is a perspective view of an embodiment of sample carrier in the form of a test strip or chip.

Referring next to FIG. 6, there is shown a preferred embodiment of sample carrier, in this example in the form of a test strip or chip 30. This is formed as a small hand-held element intended for a single use application. It is typically preloaded with the appropriate chemical elements, in this example magnetic carrier particles and labels, these being bound to antibodies for the detection of a particular antigen. For this purpose, the chip 30 is provided with a plurality of chambers within its structure, some examples of which are described below.

In this embodiment, the chip 30 includes to its casing a handle portion 32 for ease of handling by medical staff and a processing portion 34 at a front end thereof which includes a suitable port for the insertion of a specimen to be tested and for coupling into a detector, of which an embodiment is described below. Typically, the inlet port allows a sample of fluid, blood for example, to be drawn into the chambers of the device by capillary action.

The processing portion of the chip 30 is provided with an incubation chamber and a detection chamber separated by a conduit, that is having a structure equivalent to that shown in FIGS. 7 and 8 described below.

FIG. 6 also shows the chip 30 provided with a data connector 36. The data connector includes one or more devices for providing data to detector unit (described in detail below)

relating to the class and/or nature of the chip, for example the antigen the chip is arranged to test, data relating to the antigen itself, test parameters and so on. Further description of the data connector are described below.

FIG. 6 shows the data connector 36 as a separate element to the chip 30, in which case it can be coupled to a detector at any suitable port location separate from the position at which the chip is attached to the detector. It is envisaged for other embodiments that the data carrier 36 could be integrally formed with the chip 30, possibly as an integral part of the casing of the chip 30.

It is preferred that the chip 30 is made as a simple and cheap component. In one embodiment, depicted in FIG. 7, the chip is formed as a sandwich structure having a plurality of layers, among these upper and lower covers layers 40, 42. There is provided at least one central layer 44, for example of a film, having a cut out 46 providing the incubation and detection chambers 48, 50 of the device as well as a separation channel 52 therethrough. These chambers are closed off by the inner surfaces of the top and bottom elements 40, 42 of the device. The top 40 is provided with an aperture 54 therein which aligns with the channel 52 between the incubation and detection chambers 48, 50 for the introduction of a sample to be tested, as described in further detail below.

Figure 7:
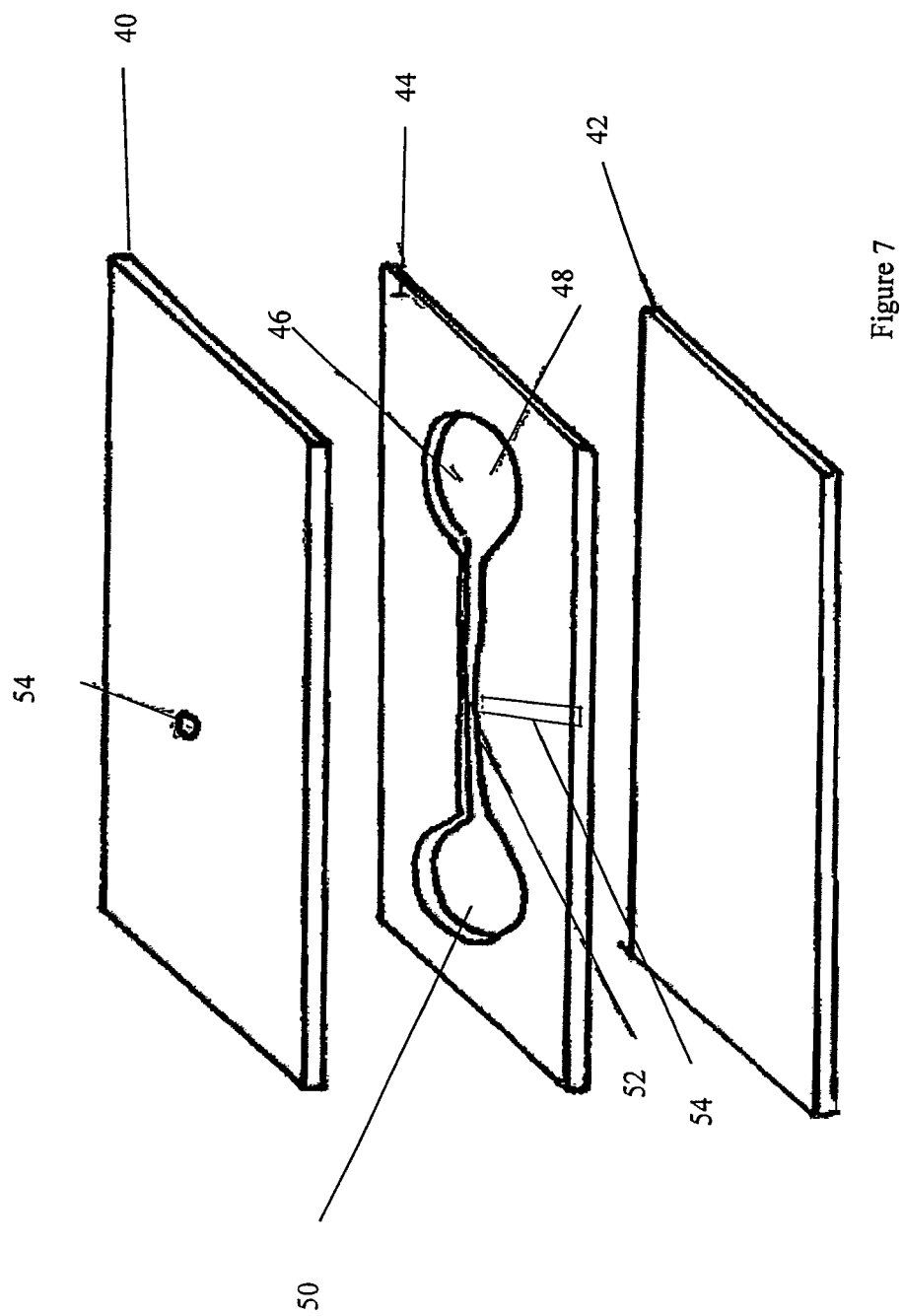
FIG. 7 is an exploded view of a practical implementation of the test chip of FIG. 6.

FIG. 7 illustrates an advantageous and convenient structure for the chip 30, which is easy and cheap to produce and which therefore can readily be provided as a single use device at little cost. Specifically, it is only necessary to provide three layers of suitable material, the top cover 40 with a suitable aperture moulded or bored therein, the middle layer with the shape of the chambers and conduit cut therein and the bottom layer. These layers can then be assembled and joined together, for example by adhesive, heat bonding or in any other suitable way, in order to create within the device 30 the fluid tight chambers and conduit. Other embodiments are, however, contemplated including, for example, forming the chambers 48, 50 and conduit 52 on an inner side of one or both of the outer layers 40, 42, in which case the device may only require two elements, the top and bottom halves 40, 42 to the casing. Of course, this would require a specific mould design rather than being able to be made from flat film, as is the case with the embodiment illustrated in FIG. 7.

It is preferred to provide to the incubation or mixing chamber 48 one or more vents to allow the escape of air during the insertion of a sample into the device. Such vents could be provided as small apertures in the upper cover 40 of the chip or as small channels in the layer 44 or in any other suitable form.

The chip 30, although preferably of a substantially flat and planar configuration, could have any other shape, particularly when it is formed of a plurality of moulded parts. A flat configuration as shown is preferred for ease of handling, correct orientation in a detector device and labelling.

In the preferred embodiments, the chip 30 is made from an inert material, including: a plastics material, glass, silicate, polysilicate, a polycarbonate, polystyrene, nylon and so on.

The schematic example shown in FIG. 7 would be complemented by a connector element for coupling to a detector device and by one or more terminals for the detection of the ions or other labels provided therein. In the preferred embodiment, and as shown in the drawings, the detection terminals 60 are electrical terminals for detecting an electrical characteristic of the sample in the form in the detection chamber. However, other types of detection terminals or probes are envisaged for detecting other parameters, such as optical terminals, resonance terminals, plasmodic terminals, vibrational (such as Raman) terminals or acoustic wave terminals.

The simplicity of the chip 30, in whatever form it is provided, enables it to be useful and viable as a throw-away item for testing an antigen. There are described below different embodiments which can provide for the testing of a plurality of antigens within a single chip.

It is envisaged that in some practical embodiments the chip 30 could be a few centimeters in length, preferably up to 10 cm, and a few centimeters in width, preferably up to 4 centimeters; and most preferably it has dimensions of around 4×2 centimeters. The chambers 48 and 50, as well as the conduit 52 and port 54, the latter where appropriate, preferably have heights of up to 1 mm and preferably between 5 µm to 500 µm. This can promote capillary action of fluid within the device 30. It is preferred that the incubation chamber 48 has a volume of around 0.5 µl to around 100 µl, most preferably from 1 to 10 µl. The detection chamber 50 preferably has a volume up to around 20 µl and most preferably from 0.5 to 5 µl. The conduit 52 preferably has a volume of 0.1 µl to 10 µl, most preferably 0.5 µl to 3 µl. The conduit 52 preferably has a length between 1 mm and 5 cm and most preferably between 0.5 and 2 cm; a width preferably of around 1 to 5 mm, most preferably of around 1 to 3 mm and in the preferred embodiment of around 2 mm.

Figure 8:
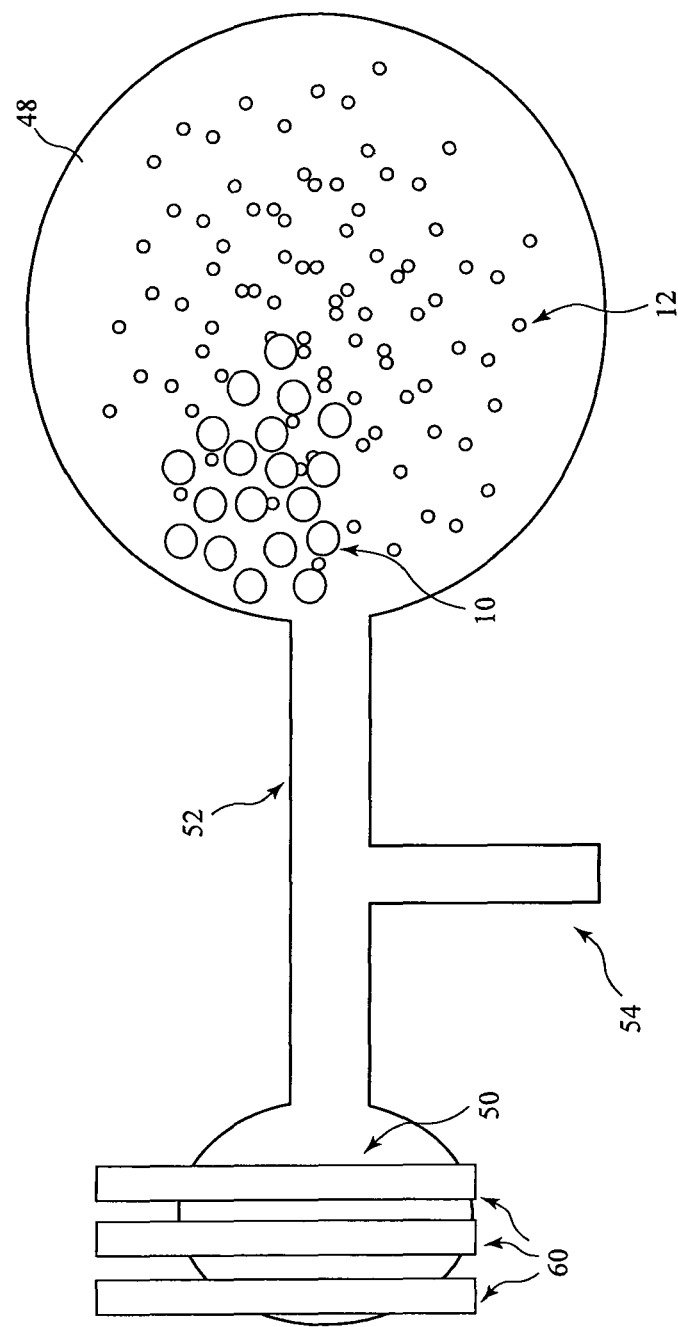
FIG. 8 is a schematic diagram of a preferred embodiment of testing chambers for the strip or chip of FIGS. 6 and 7.

Referring now to FIG. 8, there is shown a schematic diagram of the internal arrangement of the chip 30 loaded with carriers and labels, that is in a form in which it would be supplied to an end user such as a general doctor, ambulance or hospital staff.

As each chip is intended to be for a single use, it is preloaded with the elements associated with a particular antigen, that is with an inert fluid carrier of suitable form throughout the chambers and conduit of the device, with magnetic particles 10 and label particles 12 suspended in the liquid carrier, each of the particles 10 and 12 provided with the appropriate antibodies 14, 22 for the particular antigen to be tested, in the incubation chamber 48 and with, in this example, an ionising substance in the detection chamber 50.

The port 54 is coupled at a position along the conduit 52 between the incubation and detection chambers 48, 50 and is sized to draw a sample to be tested, for example in medical applications a blood, saliva or other bodily sample, by capillary action. The location of the port 54 is such that the flow of fluid into the device 30 will naturally push the elements in the chambers 48, 50 apart and thus assists in isolating the label particles 12 from the detection chamber 50 until these are carried to this as intended. This restricts unbound labels 12 from entering the detection chamber and introducing errors into the readings. When a reading is made, the amount of labels 12 is therefore reliably directly related to the number/amount of antigens sought to be detected in the original specimen.

Similarly, the conduit 52 is preferably of a size to allow passage of the combined carrier/antigen/label particles therethrough by means of in this example, an external magnetic force but insufficient for significant natural migration. In the preferred embodiment, the chip 30 is pre-loaded with the carrier and label particles 10, 12 and with the label detecting particles in the chamber 50 and these are preferably either dried or provided in a dried form for storage and transportation purposes. These particles thus remain in the chip 30 in a substantially immovable condition. The introduction of a fluid sample through the inlet 54 hydrates or otherwise causes suspension of the stored particles and allows the device 30 to perform its functions.

In an alternative embodiment, the particles stored in the chip 30 may be stored in a liquid and retained in their respective chambers 48 and 50 by means of a dissolvable or breakable barrier, typically at the part of the conduit 52 between the port 54 and the chamber 50. A breakable barrier could be breached, for example, by the magnetic particles themselves as they are transported to the detection chamber 50. In another embodiment, the conduit 52 could simply be closed, for example by resiliently pressing the walls 40, 42 together or by any suitable closure mechanism.

Thus, when a sample to be tested in fed to the port 54, this is drawn through the port into the conduit 52 and from there into the incubation chamber 48. In the chamber 48, any antigens 16 compatible with the antibodies 14 and 22 will bind to these, thus forming the complexes of carrier 10, antigen 16 and label 12. Any other antigens and substances in the sample will remain dissolved or in suspension in the carrier fluid in the chamber 48 but will not bind either to a carrier 10 or to a label 12.

If necessary or desirable, a moving magnetic field could be applied to the incubation chamber 48 in order to move the magnetic carriers 10 and thereby to stir the mixture. Such a magnetic field could be produced readily by an electromagnetic device and suitable power source, an example being a series of electrical coils suitably arranged over the chamber 48.

The introduced sample is allowed to mix in the chamber 48 for a period deemed sufficient to allow binding of the relevant antigens in the sample to the carrier and label particles 12, a process termed herein as incubation although could equally be described as bonding, combining or other suitable term.

After this incubation period, a moving magnetic field is applied over the chamber 48 and over the conduit 52, in a direction towards the detection chamber 50. This can be achieved by a suitable arrangement of electrical coils positioned over the chip, provided for example in the detector described below, and powered to provide a pulsing electromagnetic field in the direction from the chamber 48 to the chamber 50. It will be appreciated by the skilled person that these coils or a part of these coils could also be used to provide the mixing function within the chamber 48, for example by altering the current supply through the coils to generate different movements within the carrier particles 10.

The moving magnetic field produced draws the magnetic carriers 10 from the chamber 48 into and through the conduit 52, towards and then into the detection chamber 50, that is towards the left in the view of FIG. 8. Substantially all of the magnetic particles 10 will and should be drawn to the chamber 50 during this phase, including those to which no antigen has attached. However, label particles 12 which have not become attached to a magnetic carrier 10 and any other antigens and other elements in the sample will remain in the incubation chamber 48 as they will not be influenced by the magnetic force imparted to the chip.

In some embodiments, shown for example in FIGS. 40 to 47 the conduit 52 is preferably utilised as a wash zone to obstruct any unbound label, which may be caught in, the flow caused by the magnetic particles and to prevent the unbound label reaching the detection chamber 50. For this purpose the conduit can be provided with obstructions such as pillars 522, meanders 526, bumps 524 and raised features. These features can cause turbulence in the flow and aid the separation of the unbound label from the magnetic particle mix.

Figures 40, 41:
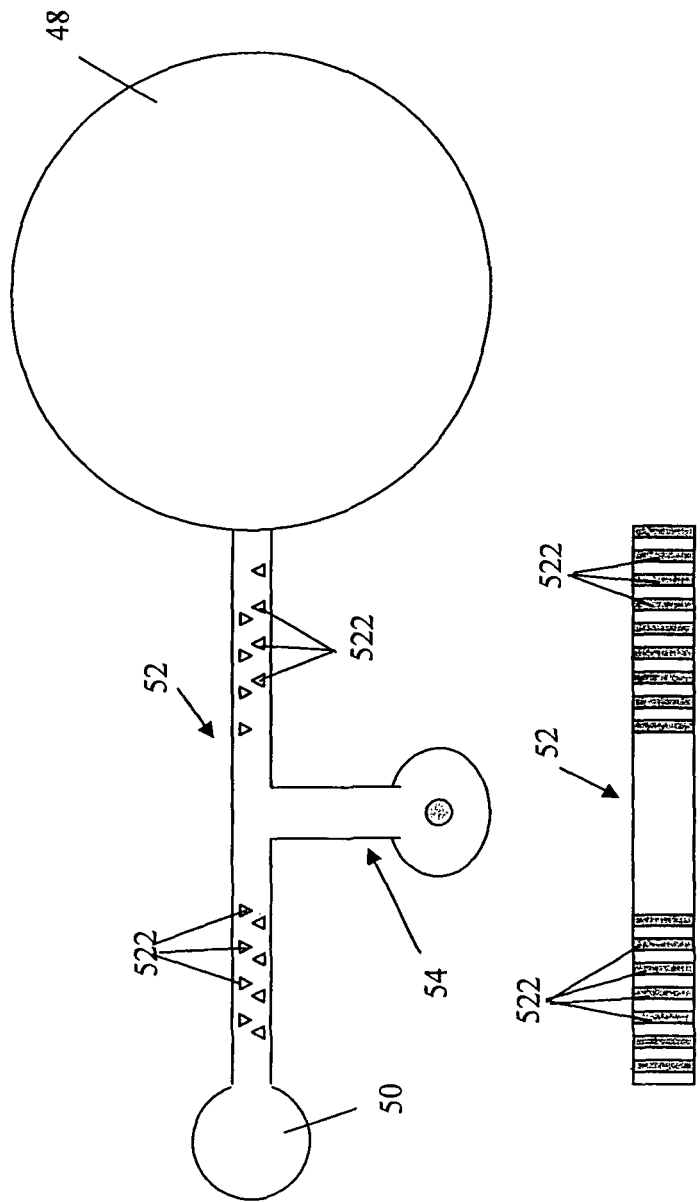
FIG. 40 is a schematic diagram of an embodiment of testing chambers for a test chip or strip with pillars in the conduit.
FIG. 41 is a side sectional view of the conduit of FIG. 40.
Figures 42, 43:
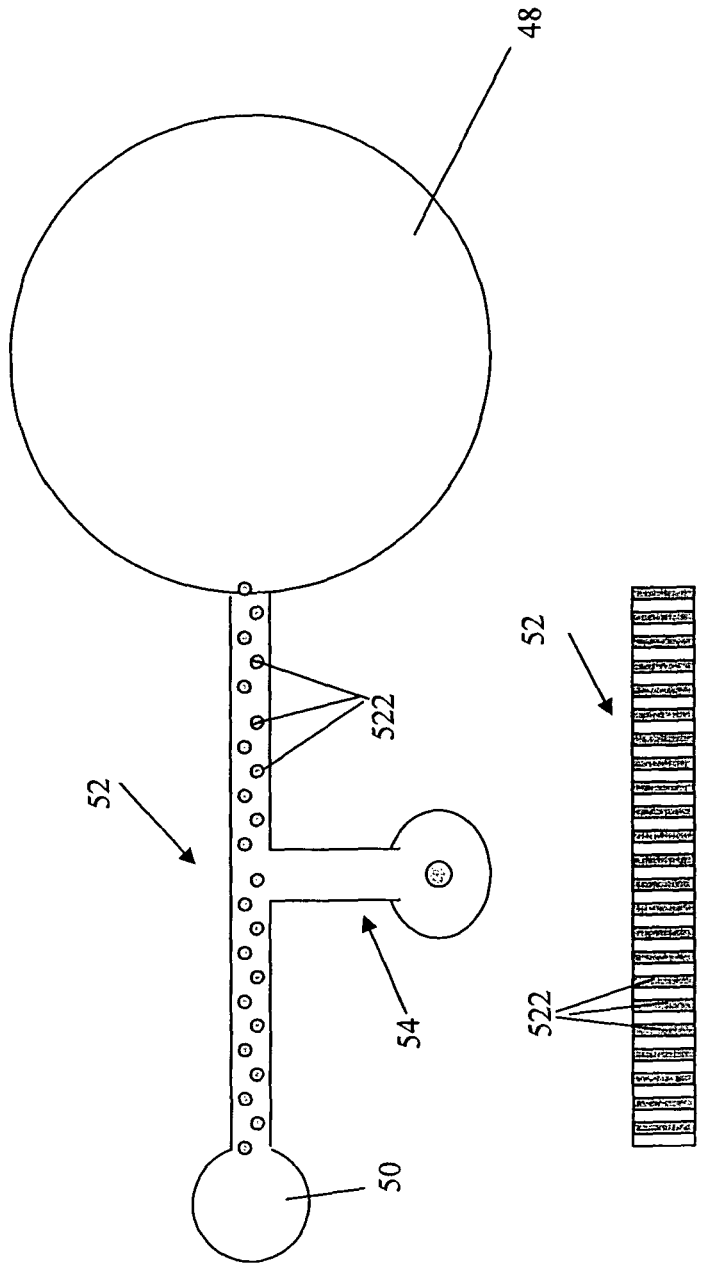
FIG. 42 is another schematic diagram of an embodiment of testing chambers for a test chip or strip with pillars in the conduit.
FIG. 43 is a side sectional view of the conduit of FIG. 42.

As shown FIG. 40, pillars 522 can have a triangular cross-section, or can have a different cross section such as circular (FIG. 42). The pillars 522 can be arranged on either side of the port 54 (FIG. 41), on only one side, or throughout the conduit 52 (FIG. 42). Preferably proximate pillars 522 are provided on opposite sides of the conduit 52 to force the flow along a circuitous route.

Bumps 524 can be provided on any side of conduit 52 to cause turbulence of the flow and aid the separate of unbound label from the magnetic particle mix. The bumps 524 can be rounded (FIG. 45) or triangular (FIG. 46) or any other shape that interferes with the flow.

Figure 47:
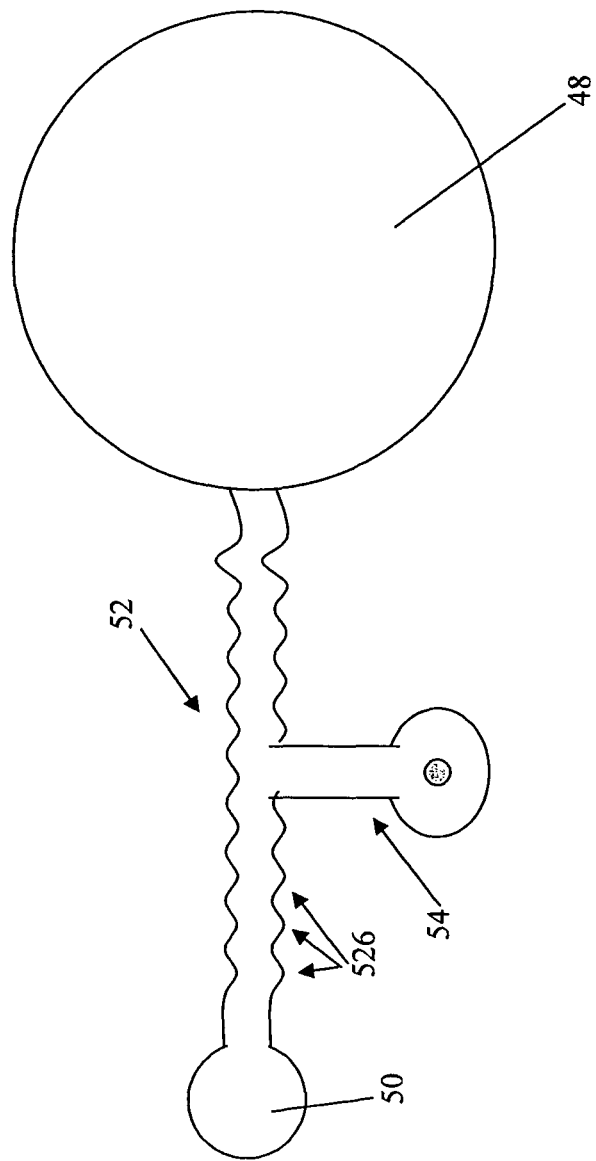
FIG. 47 is a schematic diagram of an embodiment of testing chambers with meanders in the conduit.

Meanders 526 can be provided by providing distortions in the side of the conduit 52 (FIG. 47).

The detection chamber 50 is shown provided with a plurality of electrical terminals 60, typically in the form of a plurality of strips of metal, metallic or otherwise conductive material which extend to the inside of the chamber 50 to be able to measure electrical charge or conductivity as well as, in some embodiments, to impart electrical energy to the contents of the chamber 50.

In the particular example described above, the chamber 50 is filled with ammonium thiocyanate which forms a charged surface of the silver nano-particle which can be attracted to an electrode surface and be electrochemically oxidised. In a modification, the chamber 50 can be filled with an oxidising or ionising compound able to dissolve and ionise the silver particles of the silver sol label 12. This produces a volume of silver ions in the carrier fluid in the chamber 50, in accordance with the depiction of FIG. 5. The silver ions, which are positively charged, can be attracted to the electrical terminals 60 by applying a negative potential to these, thereby providing a measurable parameter related to the existence and amount of silver transported to the detection chamber and thereby the existence and amount of the associated antigen in the original sample. The magnetic particles 10 which have not bound to an antigen will not carry any label particle 12 with them and thus will not contribute to the amount of label in the chamber 50. For the purposes of detection, therefore, they will be irrelevant.

It will be appreciated by the skilled person that the provision of electrical terminals 60 is relevant where the label 12 produces a measurable electrical parameter. Other embodiments are envisaged which provide other parameters for measurement, such as colour, illumination, translucency or opacity and any other measurable parameter. In this case, in place of electrical terminals it is envisaged that there would be provided other detection means, such as a photosensor or just a window for such a detector.

Figure 9:
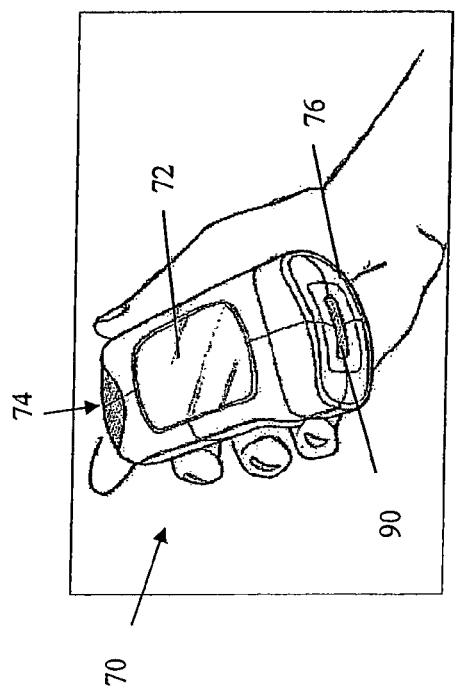
FIG. 9 is a perspective view of a preferred embodiment of hand-held testing device.

Referring now to FIG. 9, there is shown a preferred embodiment of detector unit 70. This is advantageously a hand-held self contained unit able to effect the chemical assay, to interpret the results and to display these on a display screen 72. The detector unit 70 is also provided with one or more operating buttons 74 to enable various common basic operations such as switching on and off the device, resetting the device for a new test and so on. At the other end of the device, there is provided a port 76 designed to receive a test chip 30 of the type described above.

Figure 10:
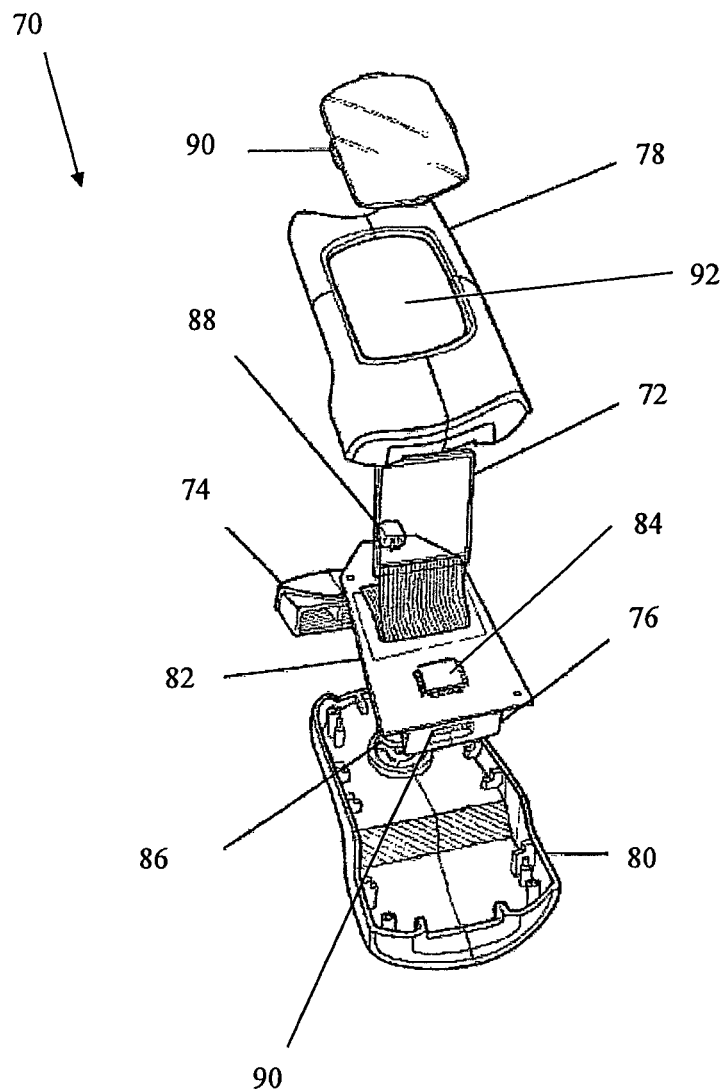
FIG. 10 is an exploded view of the testing device of FIG. 9.

FIG. 10 shows an exploded view of the detector device 70 so that the major components thereof can be seen. In this embodiment, the device 70 is formed of a plastics casing of two parts 78, 80 within which there is provided a circuit board 82 which holds the components of the device, including display screen 72, which may be an LCD screen, the connector element 76, suitable circuitry including a microprocessor or logic unit 84 and memory (only one electronic component is shown here but the skilled person will appreciate that in practice there will be a variety). In addition, the circuit board supports a battery 86 and a PCB switch 88 which cooperates with moulded button 74. A cover window 90 covers the access window 92 in the top cover half 78. It will be appreciated that the electronic components of this embodiment could be printed as well as being on a standard PCB board.

The electrical circuitry preferably also includes in an appropriate memory a database of test parameters and data for recognising the test being carried out and for interpreting the measurements as required. Such data is dependent upon the parameters being measured and their correlation with the ailment the subject of the test. The skilled person will readily appreciate the nature of this data as it forms part of the skilled person's common knowledge.

The detector unit 70 may include other components, such as a buzzer or loudspeaker for producing warning signals, connectors to computers and so on.

The connector element 76 includes electrical components suitable for imparting to the test chip 30 the magnetic field for moving the magnetic carrier particles 10 within the chip and an electrical coupling element for coupling to the terminals 60 of the chip 30 for measuring the electrical signal produced during the test. In addition to these components, the tester 70, via the connector element 76 or another separate component (not shown) is arranged to be able to receive and read the data on the data carrier 36.

Figure 11:
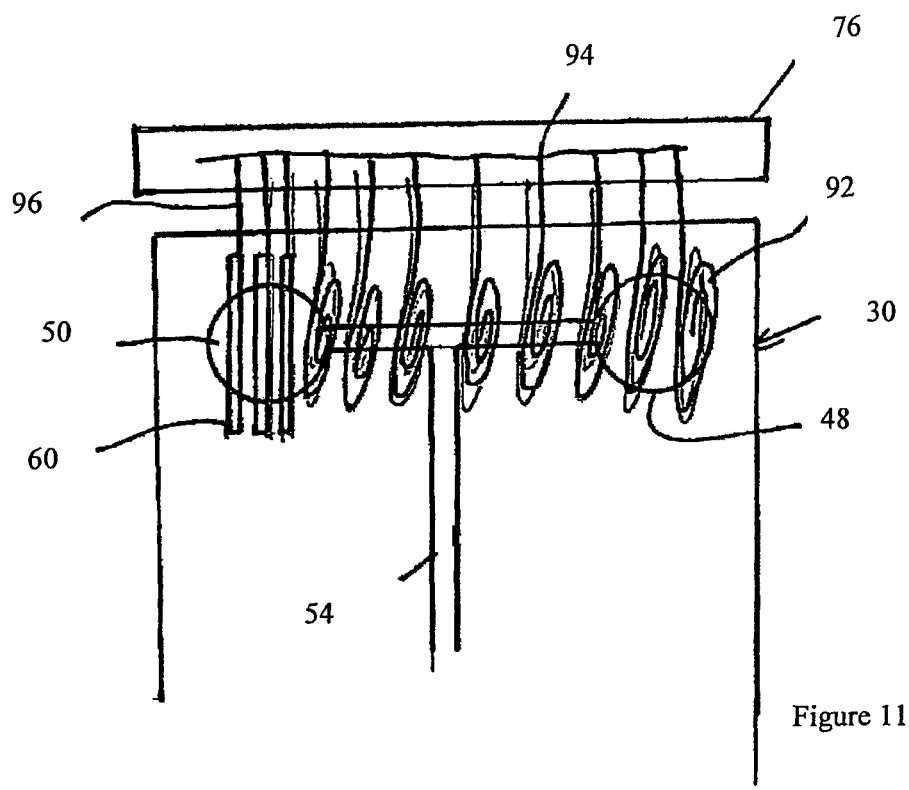
FIG. 11 is a schematic diagram showing some of the components of the detector device as they would be arranged over the test chip of FIG. 6 or 7.

An example of a suitable configuration for the connector element is shown in schematic form in FIG. 11.

The test chip 30 can be seen located below the components of the detector 70 which cooperate with the test chip 30. In particular, within the slot 90 of the connector 76 there is provided a linear array of electrical coils 92, which locate over the chambers 48, 50 and conduit 52 of the test chip 30. These are coupled through a suitable connector bus 94 to the circuitry 84 of the detector 70, in a manner which will be apparent to the skilled person. The connector 76 is also provided with a plurality of electrical terminals 96 which connect with the electrical terminals 60 of the test chip 30 and these terminals 96 are likewise coupled to the circuitry 84.

Figure 12:
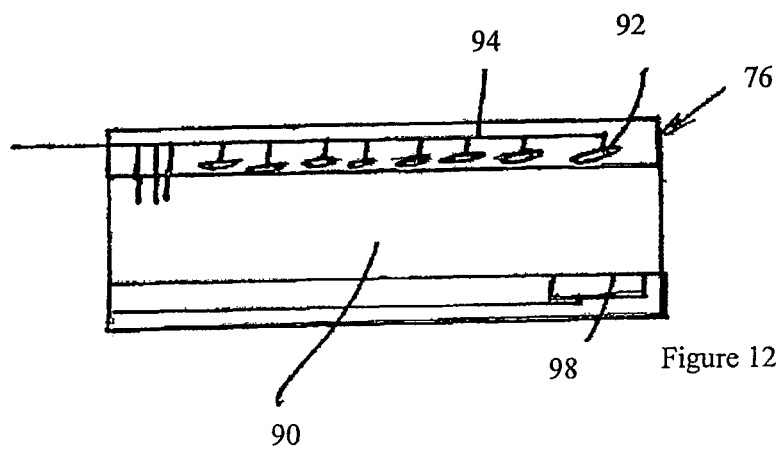
FIG. 12 is a schematic diagram in front elevation of the components of FIG. 11.

FIG. 12 shows a possible practical implementation of the elements of FIG. 11. FIG. 12 shows in schematic form and in partial cross-section a front elevational view of the connector 76. A chip 30 would slide into the connector 76 in a direction into the paper in the view of FIG. 12. Advantageously, the electrical coils 92 are embedded into the plastics structure of the connector 76, as is the electrical bus 94. Thus, when a chip 30 is inserted into the connector, the chambers 48, 50 thereof align automatically with the coil 92, as do its electrical terminals 60 with the terminals 96 of the connector 76, the latter extending into the slot 90.

In use, the electrical circuitry is operable to generate a current in selected ones of the coils 92, in so doing generating an electromagnetic field and force which passes into the chip 30. The coils 92 can be energised in one mode, and in one embodiment, to mix the elements in the incubation chamber 48 after the introduction of a sample into chip 30. Similarly, the coils 92 can be energised so as to create a travelling electromagnetic field in the direction from the incubation chamber 48 to the detection chamber 50 when it is desired to move the magnetic particles 10 to the detection chamber 50. The precise electrical mechanism for creating such electromagnetic fields are well within the ability of the appropriate skilled person.

In another embodiment, the detector unit 70 is provided with a plurality of solid magnets or solenoid magnets. These are moved across the chip 30, in a direction from the incubation chamber 48 to the detection chamber 50, in order to move the magnetic particles 10 to the detection chamber and with these the antigens and labels attached thereto. One practical embodiment provided a series of solid magnets at a periphery of a rotating disc part of which rotates over the chamber 48 and conduit 52 so as move the Magnets thereacross. Such magnets could also be moved to provide a mixing force within the chamber 48.

FIG. 12 also shows the provision of an identification detector 98 in the lower wall of the connector 76. This would be provided in cases where the chip 30 itself carries an identifier, such as a machine readable code (for example a bar code, lettering or numbering) or even a mechanical code, such as a key coding element formed within the casing of the chip 30. The detector element 98 may also provide for data transfer to the circuitry 84 in cases where the chip carries some form of electronic data, such as data relating to the test it is intended to carry out in electronic form, data relating to the test parameters.

In some embodiments it is also envisaged that the chip 30 or a dummy chip could carry updating software for the detector unit 70, which software could be downloaded through the detector element 98 in the connector 76 or an equivalent element provided elsewhere on the casing of the unit 70. This would provide a convenient and efficient method of updating the device 70 with data relating to a new test to be carried out, such as to detect a new antigen or other medical condition, as well as to provide general software updates. The unit 70 could therefore be kept constantly updated without the need to service the device elsewhere.

It is envisaged in some embodiments that the chip itself could be an "intelligent" chip, that is the chip could carry the data required for identifying the test it is designed to carry out and to provide the data for interpreting the results of any measurements taken by the unit 70. In this case, the detector element 98 and the circuitry 84 are designed solely to read data from the chip 30 and, as appropriate, to interrogate this to obtain the required data.

Figure 13:
FIGS. 13 to 22 are diagrams representative of one example of application of the devices of FIGS. 6 to 12.
Figure 15:
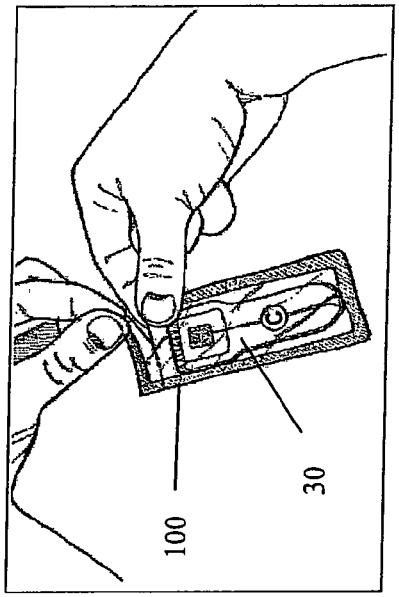
Figure 14:

Referring now to FIGS. 13 to 22, there is shown an example of a use of the chip 30 and detector device 70 in a medical application, for example by a nurse of physician for diagnosis on a patient, as shown in FIG. 13, or by a patient personally, as shown in FIG. 14.

The chip 30 is provided in a sealed pouch 100 which in this embodiment is provided with a clear front window to allow sight of the chip 30, useful in cases where the chip carries markings on it such as the type of the chip 30.

Figure 16:
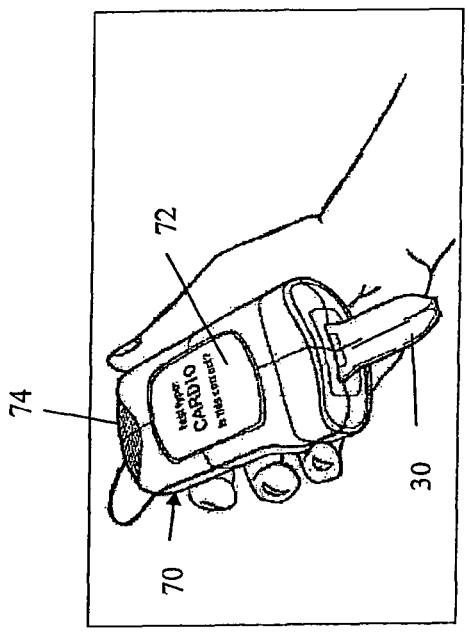
Figure 17:
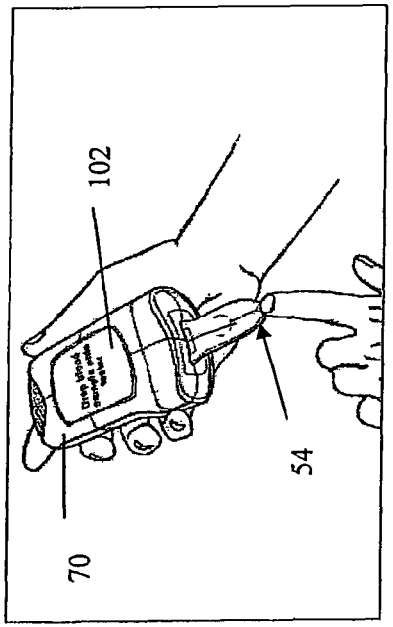

It is preferred, as shown in FIGS. 16 and 17, that the chip, once removed form the pouch 100, is checked in the tester 70 to ensure that it is the correct chip for the test to be preformed. For this purpose, the detector 70 can be made to read the identifier on the chip 30 and to display an indication of the test, which the chip 30 is designed to be carried out. In this example, the chip 30 is designed to carry out a cardio performance check on a patient. In this case, the test might look for a change in one of the following indicators of cardiac malfunction such as myglobin, troponin-I or T, NT-pro-BNP (Brain Nutreated protein) or straight BNP; for which the binding elements 14, 22 of the carrier particles 10 and the labels 12 have appropriate moieties, such as antibodies, mimitopes or DNA or RNA.

Once the user has ascertained that the chip 30 is the correct one, the test sequence is initiated by appropriate depression of the button or buttons 74. Advantageously, the unit 70 then guides the user through the various steps of the procedure by suitable instructions on the display 72.

Figure 18:
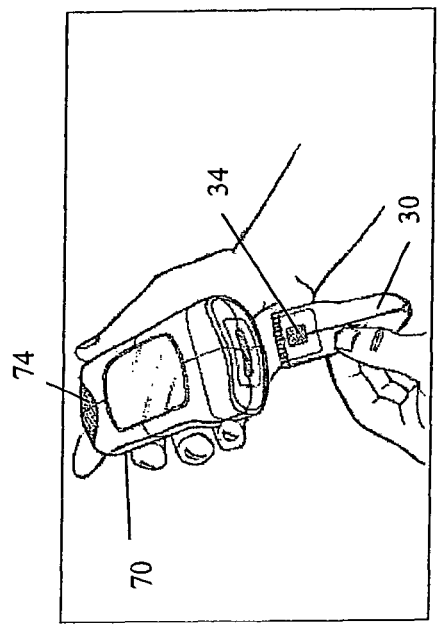
Figure 19:
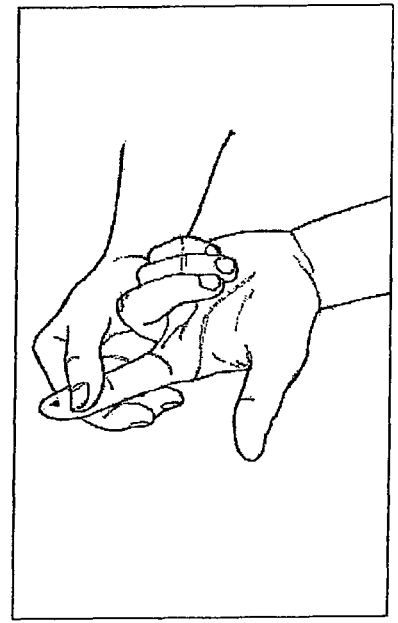
Figure 22:
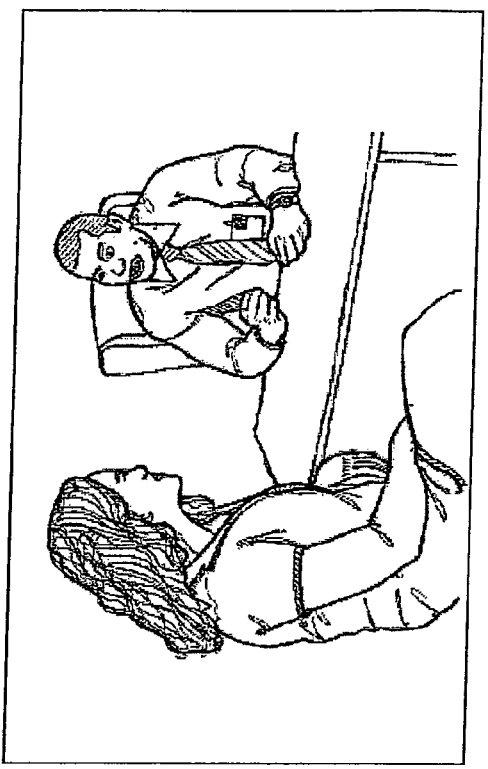

The first step of the procedure, in this particular example, is for the patient, or carer, to obtain a blood sample form the patient, typically by a pin prick, as shown in FIG. 18.

In this embodiment, the chip 30 is provided with its port 54 at the end thereof, in which case the port is coupled through an elongate conduit 102 to the conduit 52 between the chambers 48 and 50 of the device. Advantageously, in this example, the chambers 48 and 50 would lie cross-wise at the end 34 of the chip 30 and thus wholly within the connector 76 of the device 70, as will be apparent in particular form FIGS. 17 and 19.

Figure 20:
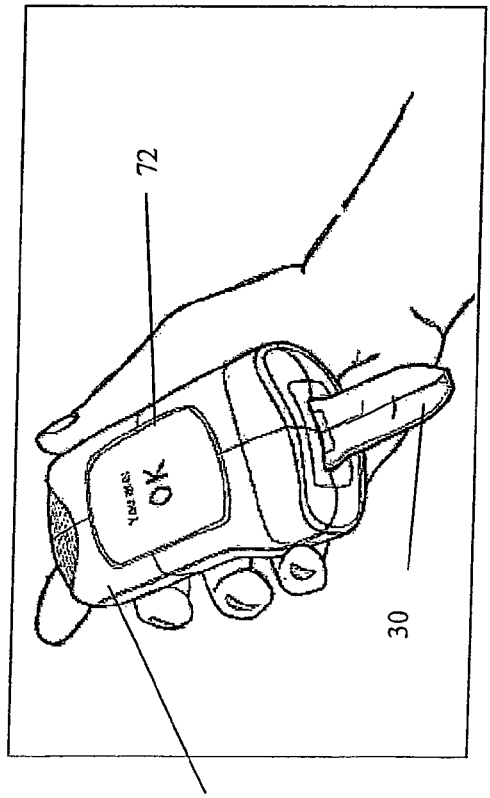
Figure 21:
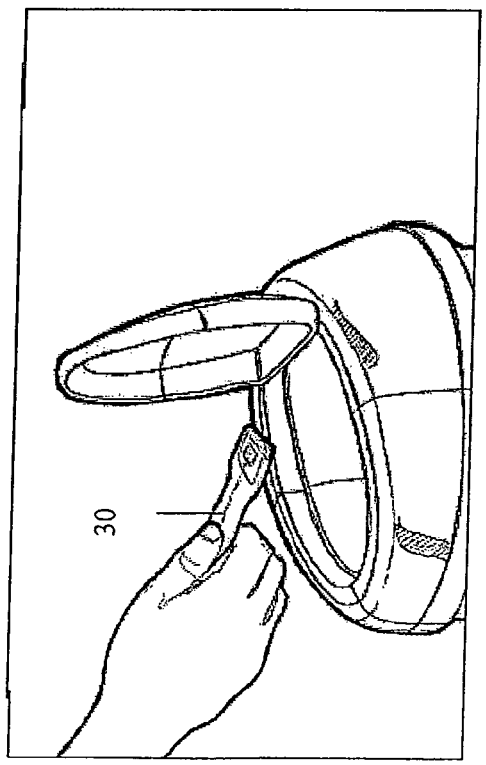

Once the user has deposited a blood sample into the chip 30, the device 70 can be operated, again by suitable depression of the button or buttons 74, or simply after a predetermined time period, to commence the mixing and transport phases within the chambers 48 and 50 and then to take a reading through the electrodes 60 and 96. The unit 70 will then determine whether or not the patient possesses the antigens for which the test was carried out and therefore the associated medical condition. In the example of FIG. 20 the device 70 is designed to display a simple positive or negative determination to the test, that is whether the patient does or does not have the particular ailment. In other embodiments or medical tests, the unit 70 can be arranged to give an indication of the quantity of the parameter tested, for example the level of antigens and thus seriousness of the ailment.

Detection of the ions in the detection chamber 50 can be effected in a variety of manners, the detector unit 70 not being specific to any one of these tests. In one example, the detector unit 70 is operable to apply to one of the electrodes 60, that is a working electrode, a positive voltage which attracts the ions, causing these to migrate to or concentrate on the electrode and in effect to plate this with ions. After a suitable time period, the polarity of the working electrode is reversed, causing the ions to be stripped off in an ion cloud. The concentration of ions is detected by measuring the current through the other two electrodes over this sweeping voltage. There are provided in this embodiment two other electrodes, one being a counter electrode and the other a reference electrode. In the case of a very small chip 30, however, there may be provided only two electrodes, it not being necessary to have a counter electrode.

After the test, the chip 30 can be discarded with other medical waste. As none of the sample tested comes into contact with the unit 70 during the test, the unit 70 is immediately ready for carrying out other tests.

The device and chip, in being able to test for a single element and requiring only a small sample for analysis, are able to provide a result much faster than more complex test systems and methods. Therefore, a physician such as a general practitioner could carry out the test during a medical examination and has the results of that test virtually immediately, thus being able to offer the patient immediate and appropriate medical treatment. This can be particularly useful in many applications and can save the days it can sometimes take to receive the results of medical tests. One example is in detecting whether a patient has been infected with a particular virus such as a new strain of influenza; measles, meningitis or other. In such a circumstance, the general practitioner could be provided with a selection of different chips 30 and is able within the one consultation to test the patient until the virus the patient has is identified. The patient can then be given the correct medical treatment immediately.

In prototype testing it has been found that the test can be carried out in a matter of minutes, in some cases a few tens of seconds, compared to hours and longer with traditional testing systems.

Moreover, as the sample chip 30 tests only for a single specific condition or infection, it is cheap to produce and it is therefore economically and practically feasible for single use applications. In addition, assays are not wasted where only a single condition is to be tested, as would be the case with a 'laboratory-on-a-chip' which might test for five or more conditions simultaneously. A further advantage of having each sample chip 30 testing for a single specific condition is that it is not necessary to perform a complex analysis of conditions or infections.

Figure 23:
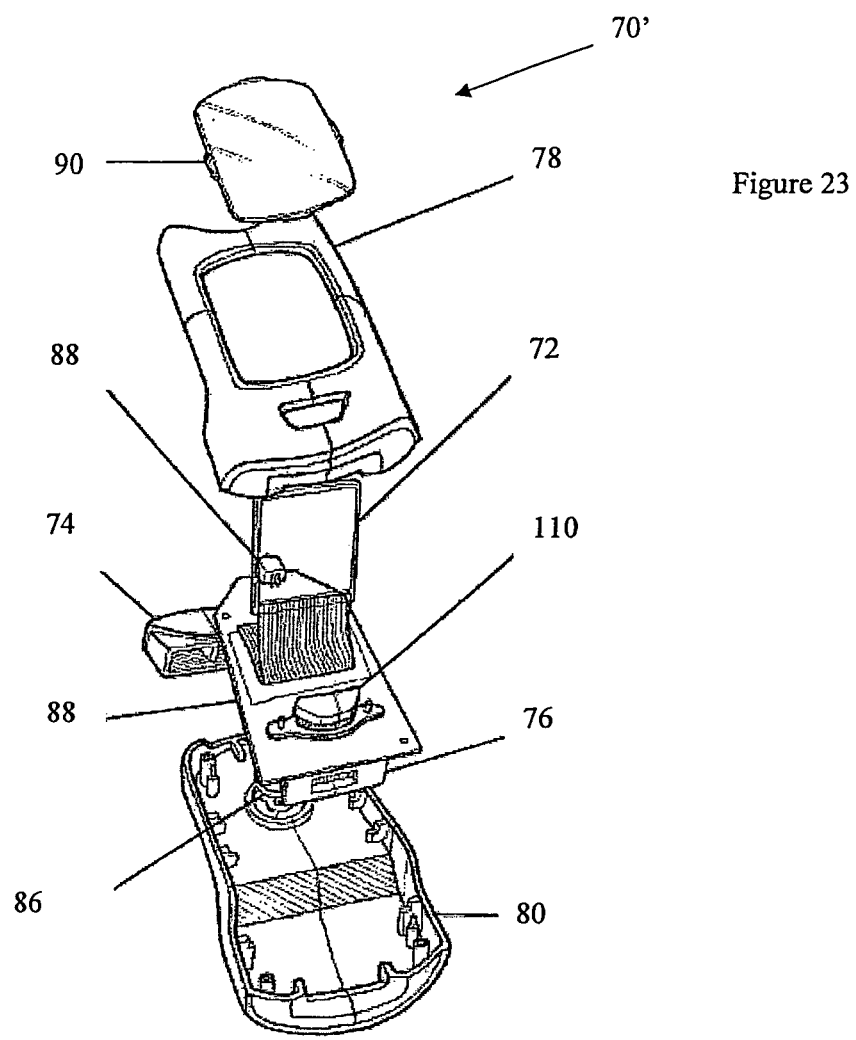
FIG. 23 is an exploded view of another embodiment of detector device.

Referring now to FIG. 23, there is shown another embodiment of detector unit 70' similar to that of FIGS. 9 to 20 and described above. It differs in that it comprises a communication button 110 and a wireless communication device (not shown). The purpose of these two features is that when the assay is complete, the user activates the communication button 110 which in turn actuates the device 70' to transmit the results of the assay wirelessly, using the wireless communication device, to a separate terminal. The data can be sent in computer processable form in a secure transmission. The terminal may be at the office of the patient's doctor, for instance if the doctor has supplied the patient with the diagnostic unit 70' for regular testing. Alternatively, the terminal may be the central database at a hospital so that the patient records can be kept up-to-date. The data may be available for access by a plurality of authorized users.

This embodiment can also be very useful to a paramedic. Communication with a hospital not only allows this to be given advance warning of what treatment will be required when the patient arrives but also enables a more thorough and reliable diagnosis to be made, since the hospital database will contain details of previous assays and prior conditions of the patient. Such advance communication to a hospital can be of huge benefit in cases where a patient needs urgent medical attention, in which can diagnosis can be carried out during transit to the hospital so this can be prepared with the correct treatments the moment a patient arrives. An example where such advance diagnosis can be crucial is in the case of myocardial infarction, where the faster a patient can be treated the greater is the risk of avoiding long term damage. In addition, such in situ diagnosis as is possible with such a device will allow paramedic staff to effect some metical treatment on site or during transit to a hospital, again very useful in cases where a patient would benefit form early medical treatment. At present, in light of the lack of diagnostic facilities of this kind in ambulances and other paramedic vehicles, such advance treatment is not possible.

Figure 24:
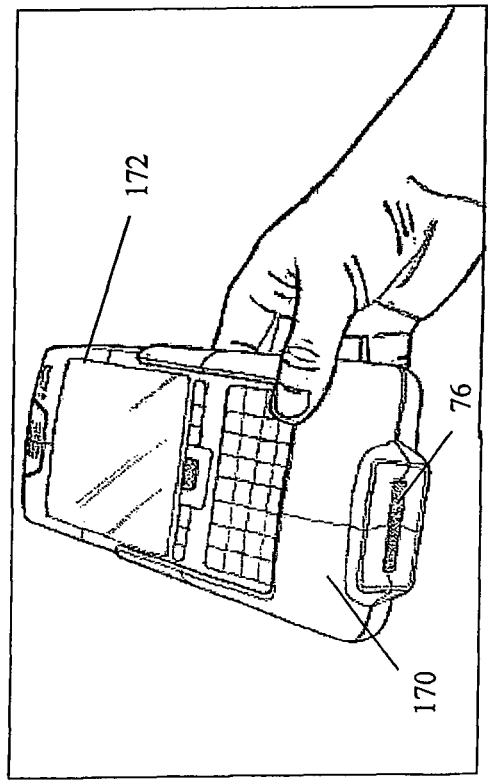
FIG. 24 is a perspective view of an embodiment of cradle detector device suitable for attachment to a hand-held computing device or other personal digital assistant.
Figure 25:
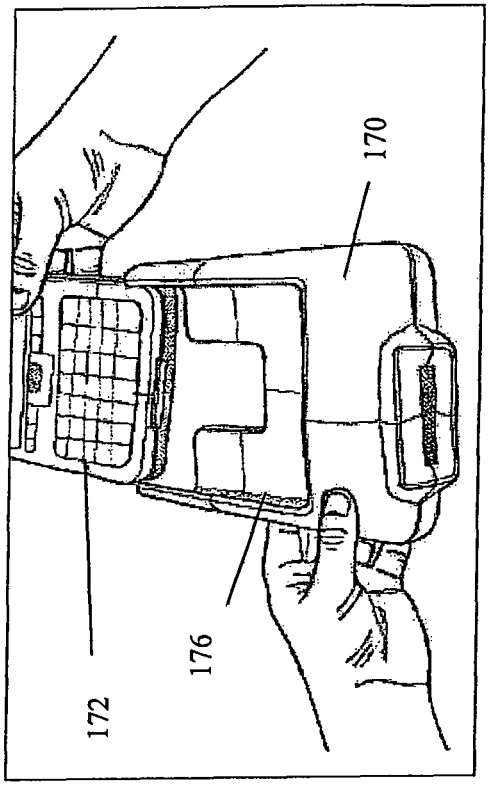
FIG. 25 is a perspective view of the device of FIG. 24 showing the cradle separated from a personal digital assistant engageable therewith.
Figure 26:
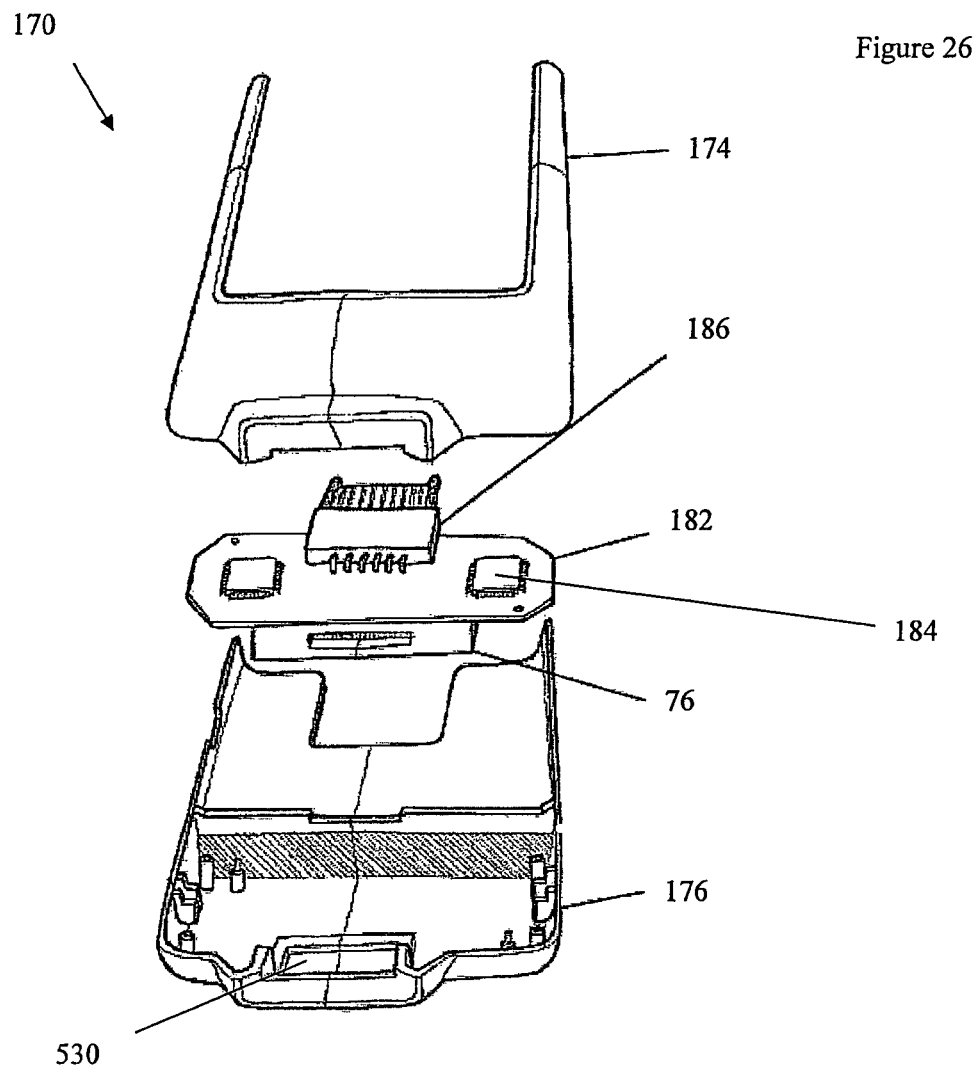
FIG. 26 is an exploded view of the cradle of FIGS. 24 and 25 showing the major components thereof.
Figure 30:
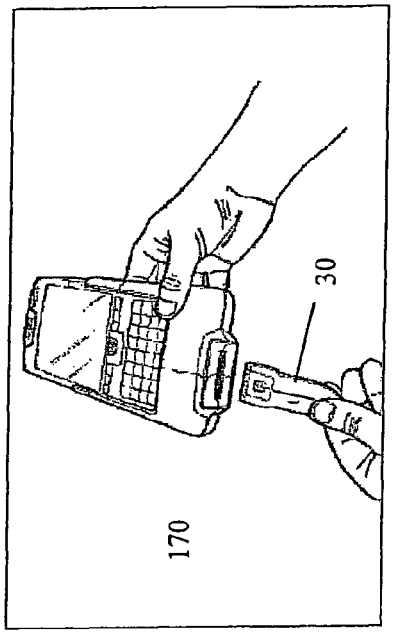
Figure 32:
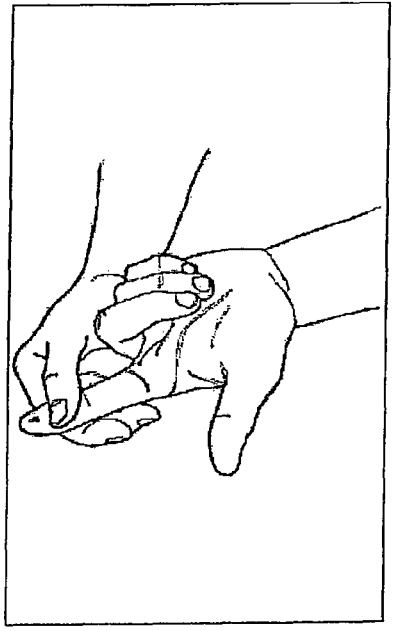
Figure 29:
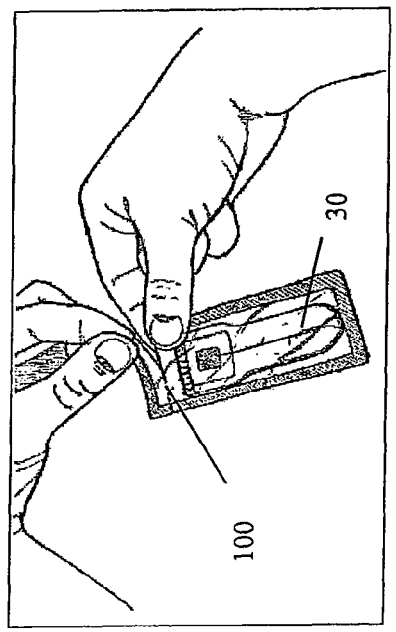
Figure 31:
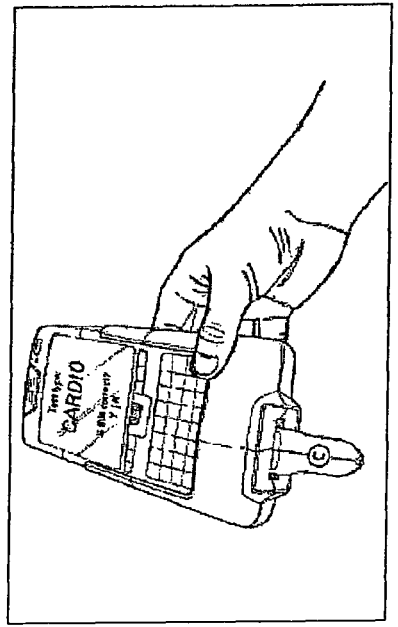
Figure 33:
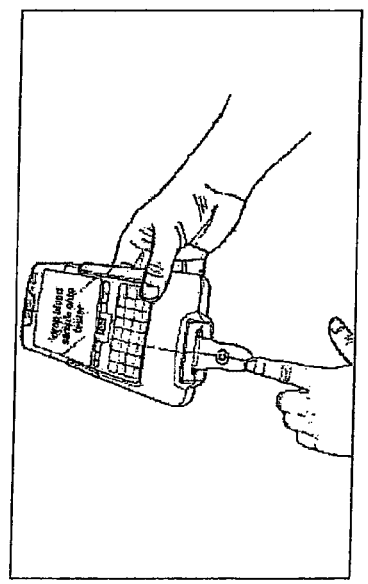
Figure 34:
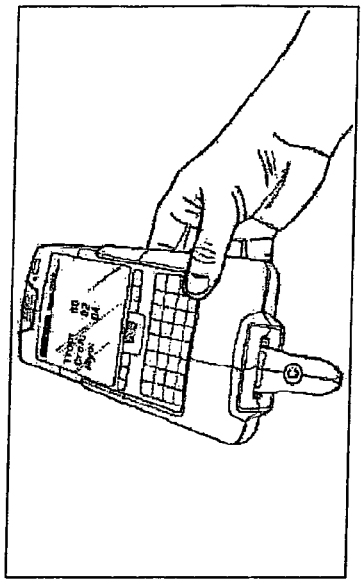

Another embodiment of diagnostic unit is shown in FIGS. 24 to 26. FIG. 24 shows a diagnostic unit 170 for connection to a personal digital assistant (PDA) 172, of a type typically used by hospital and other medical personnel. The unit 170 includes a casing having an upper half 174 and a lower half 176 which are shaped to provide a cradle chamber 176 for holding a compatible PDA 172. The unit includes a circuit board 182 supporting circuitry 184 and a connector 176, all of which are analogous to the equivalent elements of the embodiment of detector 70 described above. In this embodiment, the device 170 may be powered from the power supply of the PDA 172 and therefore need not be provided with its own battery, although some implementations might provide for this. The circuit board 182 also supports a connector 186 compatible with a corresponding connector on the PDA 172.

It is envisaged that the cradle detector 170 of FIGS. 24 to 26 could either be an intelligent device which uses the PDA 172 as a dumb terminal or could be simply an interface to the PDA 172, in which case the PDA 172 is provided with software appropriate to drive the cradle unit 170 and to analyze the readings obtained therefrom. The choice will generally be a personal choice of a supplier of these devices and, in some instances, of the user.

The unit 170 is preferably configured so that the roles previously performed by the moulded button or buttons 74 and the display 72 (as well as the communication button 110 of the embodiment of FIG. 23) are performed by the PDA device 172.

An example of usage of the cradle-type device 170 of FIGS. 24 to 26 is shown in FIGS. 27 to 36.

Figure 27:
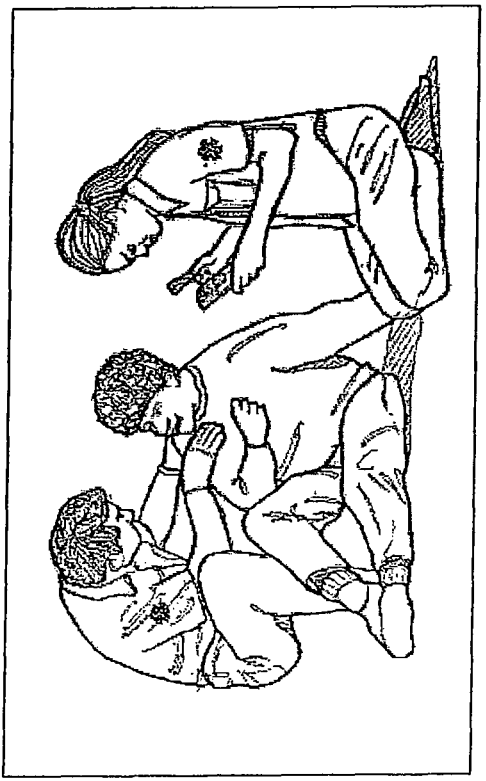
FIGS. 27 to 36 show an example of usage of the device of FIGS. 24 to 26.
Figure 28:
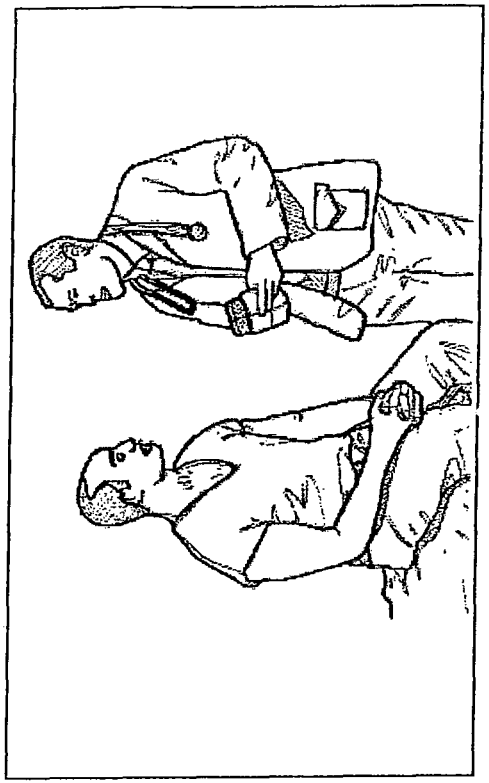

As can be seen in FIG. 27, the device is being used to attend to a person who has collapsed in the street, that is by a paramedic. On site, the paramedic can insert her PDA 172 into the cradle 170 before selecting one or more chips 30 to test for one or more possible causes of the patient's ailment. In FIG. 28, the cradle-type device 170 is being used in a hospital environment by a medical consultant.

Figure 35:
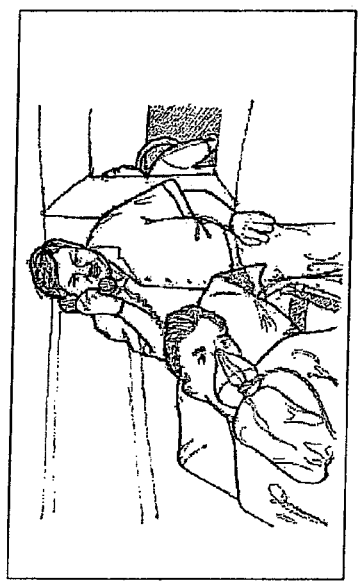
Figure 36:
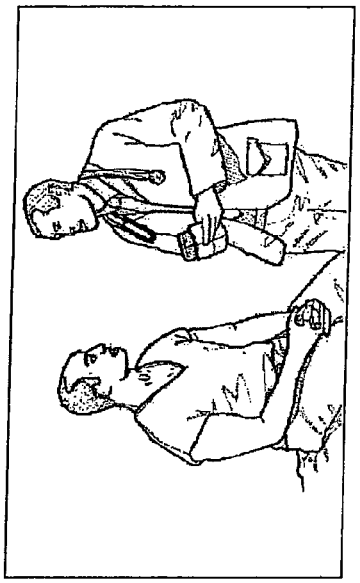

The mode of operation of the device 170 is equivalent to the embodiment 70 described above, as will be apparent form FIGS. 29 to 34. In FIG. 35, the system is shown being used during transportation of a patient to a hospital, in which the paramedic has carried out a diagnosis and, in this example, is in the process of contacting the hospital to warn it of the patient's condition and, where appropriate, to receive instructions for carrying out preliminary medical treatment on the patient before arrival. This can save critical time in treating the patient, useful in many procedures including myocardial infarction.

Similarly, in some cases the paramedic may be able to ascertain that the patient does not have a medical condition which requires hospital treatment, in which case the patient can be taken straight home for recovery, saving valuable hospital resources.

Of course, being able to attach the detector device 170 to a PDA 172 means that the medical staff can have to hand the facilities and data from their conventional PDA's, functionality with which they are accustomed and are not required to transfer data from one device to another. Instead, they can keep all of their data on their PDA device 172 and simply dock it into the diagnostic unit 170 to carry out a test. This also allows the medical practitioner to have ready access to the patients' medical data.

Figure 37:
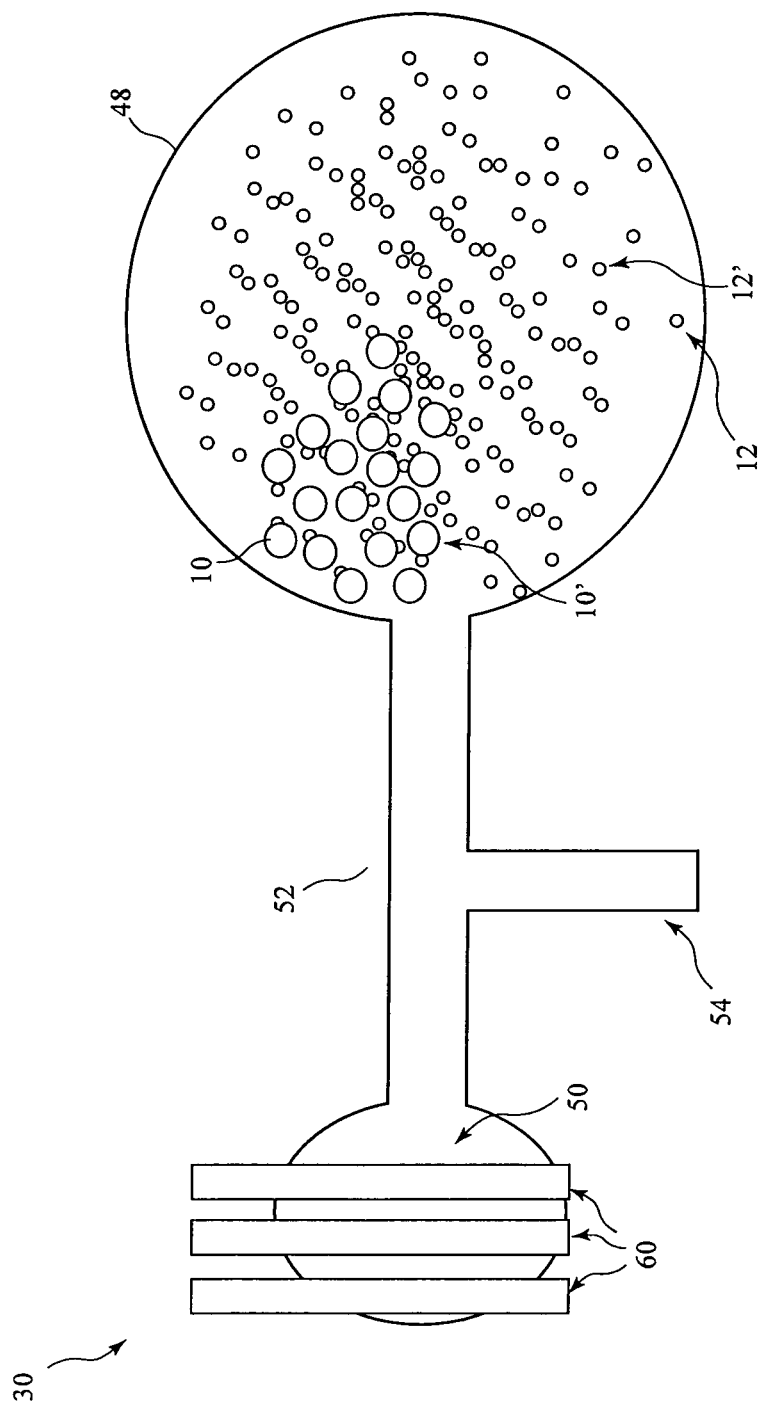
FIG. 37 is a schematic view of the chambers and conduit of a test chip 30 provided with another example of contents.

Referring now to FIG. 37, there is shown a view of a test chip 30 similar to that of FIG. 8. The difference lies in the contents of the chip, in particular in the induction chamber 48. In this embodiment, the contents in the chamber 48 is provided with two different label particles 12, 12', which may for example be of different metals such as silver, gold, copper, zinc, lead and so on, or particles loaded with a redox species such as an aromatic compound or dye. Any type of label particles 12, 12' could be used as long as these allow for detection by different means or attachment to carrier particles 10, 10' which can be transported by different mechanisms. In the case of labels which provide different measurement characteristics, these could for example be silver and gold, which can be detected by known methods. In an alternative, one of the label particles could be of a type which provides a measurable electrical parameter while the other a measurable optical parameter. Any combination of labels could be used.

In the embodiment of FIG. 37, the different label particles 12, 12' are provided with antibodies specific to a particular antigen each. The magnetic carrier particles 10 are identical in their magnetic parts but have different antibodies such that they connect to respective antigens.

Therefore, at incubation, antigens of a first type become bound to a first label 12 and a first magnetic support 10, and antigens of a second, type become bound to a second label 12' and a second magnetic support 10'. After incubation, the magnetic particles 10, 10' are drawn to the detection chamber 50 and analysed in accordance with the appropriate analysis method for the label attached to them.

For this purpose, a detector unit 70, 170 would be provided with a plurality of sensors, one for each type of label used.

Since the labels 12, 12' are both initially provided in the incubation chamber 48 with the port 54 coupled between the incubation and detection chambers 48, 50, flow of fluid into the device 30 will still push the elements in the chambers 48, 50 apart and isolate both labels 12, 12' from the detection chamber 50 so until these are carried to this as intended.

It will be apparent that the embodiment of FIG. 37 could be used to test for more than two antigens or other elements in a sample, by appropriate provision of different libel particles and connector elements (antibodies in the case of antigens).

Figure 38:
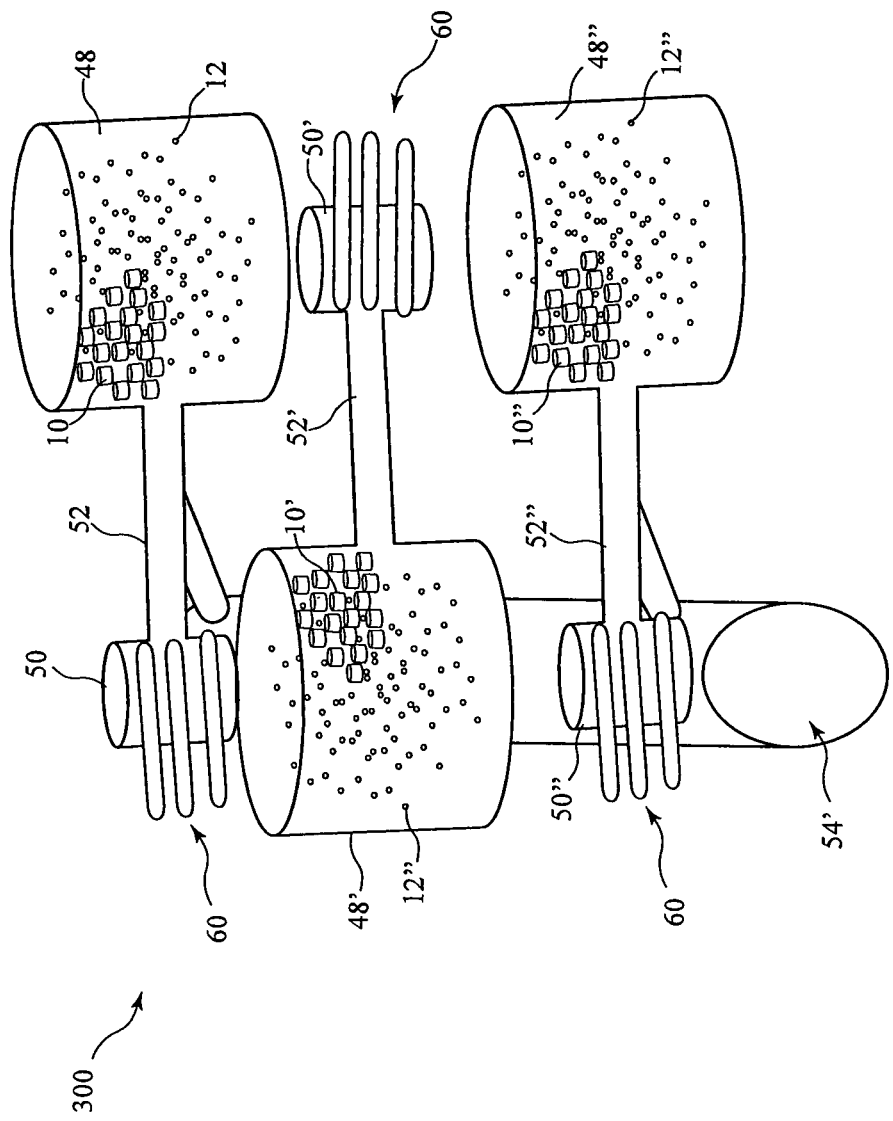
FIG. 38 is schematic diagram of another embodiment of chamber arrangement for a test chip or strip.

Referring next to FIG. 38, there is shown an embodiment of chip 300 suitable for testing separately for three different antigens from a single sample, for example. This embodiment provides a stack arrangement of different sets of chambers and connecting conduits 48-50, 48'-50' and 48"-50" each provided with magnetic carrier particles 10, 10' and 10" and labels 12, 12' and 12". A common feed port 54 is coupled to each of the conduits 52 in each case between the incubation chamber 48, 48', 48" and the detection chamber 50, 50', 50" to feed a part of a collected sample into each of the test zones in such a way to push apart elements in the incubation chambers 48, 48', 48" and detection chambers 50, 50', 50". In this way, each test zone can test for a particular antigen, by means of appropriate antibodies on the magnetic and label particles, while keeping these separate form one another, thereby allowing for use of the same label type, for example silver sol.

The embodiment of FIG. 38 can be readily manufactured using a sandwich, arrangement of planar layers similar to that shown in FIG. 7. In this case, a series of perforated layers 44 is located between a series of imperforate layers (not shown) apart from apertures linking the port 54 to each of the conduits 52. Any number of such layers 44 could be provided so as to test for any number of elements.

Figure 39:
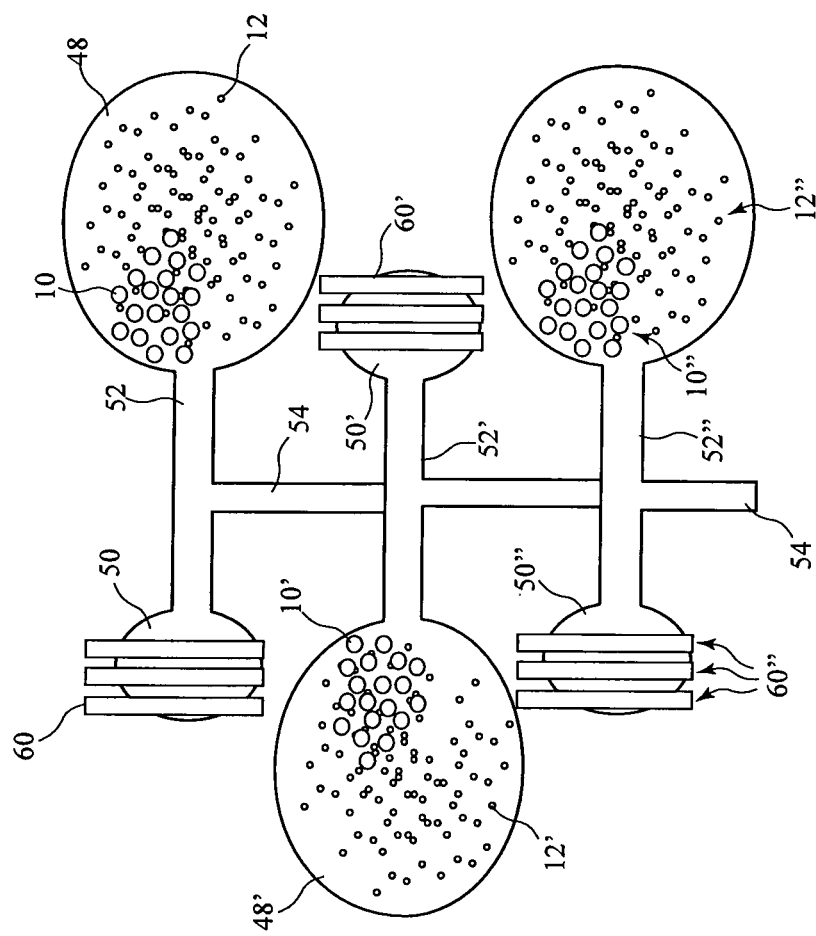
FIG. 39 is schematic diagram of another embodiment of chamber arrangement for a test chip or strip.

FIG. 39 shows another embodiment of chamber design, in this case being a planar configuration in a single layer. The structure is such that there are provided three sets of incubation and detection chambers 48-50, 48'-50' and 48"-50" coupled to a common feed port which connects to the three conduits 52, 52' and 52" in each case between the incubation chamber 48, 48', 48" and the detection chamber 50, 50', 50" in such a way to push apart elements in the incubation chambers 48, 48', 48" and the detection chambers 50, 50', 50". The arrangement can be readily produced by cutting a corresponding shape in the middle layer of a sandwich design similar to that of the embodiment of FIG. 7.

This design also allows for testing of three different elements, such as three different antigens.

In both of the embodiments of FIGS. 38 and 39 it is preferred that the detector unit, which would be provided with three connector elements for coupling to each of the terminal sets 60, 60', and 60", may be independently controllable.

Although the above described embodiments are directed to medical applications, the devices and test methods taught herein are not limited to such. They could equally be applied in the testing for numerous other applications including, for example, environmental testing of water pollution, air composition. The list is not limited.

Moreover, other release agents such as thiol with a charged unit may be used in place of the ammonium thiocyanate.

As indicated above, the detector unit does not need to be provided with the software necessary to run the assay. Instead, the test chip itself can be provided with a smart card for other device which can provide the information and in some instances the control for the detection unit.

The above-described embodiments show a sample carrier 10 which is in the form of a closed casing. It is envisaged also that there could be an open device. In one example, the sample carrier is in the form of a substantially flat structure provided with a series of zones made or of coated with a hydrophilic substance providing the chambers 48 and 50 and conduit 52 (the inlet 54 possibly being a zone of the conduit 52 but always being between the chambers 48, 50), and surrounding zones being made of or coated with a hydrophobic substance. In another example, the chambers 48 and 50 and conduit 52, optionally the inlet 54, are formed as depressions in a substantially planar substrate.

Features of the above embodiments and modifications can be combined and interchanged as required.

The invention claimed is:

1. A sample carrier formed for use in testing for the presence of a substance in a sample, including: a sample support element; a mixing zone and a detection zone within or on the sample support element, the mixing zone being pre-loaded with carrier elements and label elements, the carrier elements being movable from the mixing zone to the detection zone; a coupling channel between the mixing and detection zones operable to provide for the transfer of the sample to be tested into the mixing zone, and for the transfer of reagents between the mixing and detection zones; and an inlet for the sample to be tested within or on the sample support element coupled to the channel between the mixing and detection zones, wherein the inlet and the coupling channel are configured to draw the sample to be tested into the mixing zone.

2. A sample carrier according to claim 1, wherein the inlet is coupled to the channel between the mixing and detection zones such that flow of sample fluid into the sample carrier pushes apart elements in the mixing and detection zones.

3. A sample carrier according to claim 1, wherein the channel provides for movement of liquids therethrough by capillary action.

4. A sample carrier according to claim 1, wherein the carrier is substantially flat and/or is formed as substantially planar structure.

5. A sample carrier according to claim 1, wherein the sample support element forms a wall of a casing.

6. A sample carrier according to claim 5, wherein the casing is formed as a sandwich structure including first and second cover layers and at least one intermediate layer having recesses or apertures therein for providing the mixing and detection zones and coupling channel, one of the first and second cover layers providing the inlet port to the conduit.

7. A sample carrier according to claim 6, wherein the first and second cover layers provide opposing walls to the mixing and detection zones and coupling channel.

8. A sample carrier according to claim 1, wherein the sample support element includes a plurality of hydrophilic regions providing the mixing and detection zones, the coupling channel and inlet.

9. A sample carrier according to claim 1, wherein the sample support element includes recessing providing the mixing and detection zones, the coupling channel and inlet.

10. A sample carrier according to claim 1, including at least one detector terminal arranged in communication with the detection zone.

11. A sample carrier according to claim 10, wherein the at least one detector terminal includes an electrical terminal.

12. A sample carrier according to claim 10, wherein the at least one detector terminal includes an optical terminal, a resonance terminal, a plasmodic terminal, a vibrational terminal or an acoustic wave terminal.

13. A sample carrier according to claim 1, including an identifier element.

14. A sample carrier according to claim 13, wherein the identifier element is operable to identify a category of the carrier, and/or includes a coding unit.

15. A sample carrier according to claim 13, wherein the identifier element includes a memory element operable to provide data related to the test associated with the sample carrier.

16. A sample carrier according to claim 15, wherein the memory element includes data transferrable to a tester unit associated with the sample carrier.

17. A sample carrier according to claim 1, wherein the mixing zone is loaded with a fluid provided with the carrier elements and label elements.

18. A sample carrier according to claim 17, wherein the detection zone is loaded with a label detecting element.

19. A sample carrier according to claim 18, wherein the label detecting element is operable to ionise the label elements and to generate therefrom ions measurable by electrical detection.

20. A sample carrier according to claim 1, wherein the carrier is a single use device.

21. A sample carrier according to claim 1, wherein the coupling channel is substantially straight from the mixing zone to the detection zone.

22. A sample carrier according to claim 1, wherein the mixing zone is pre-loaded with the carrier elements and label elements in a dried form.

23. A sampler carrier according to claim 17, wherein the carrier elements and label elements are retained in the mixing zone by a dissolvable or breakable barrier.

24. A combination of a test device and a sample carrier, the sample carrier being formed for use in testing for the presence of a substance in a sample and including: a sample support element; a mixing zone and a detection zone within or on the sample support element, the mixing zone being pre-loaded with carrier elements and label elements, the carrier elements being movable from the mixing zone to the detection zone; a coupling channel between the mixing and detection zones operable to provide for the transfer of the sample to be tested into the mixing zone, and for the transfer of reagents between the mixing and detection zones; and an inlet for the sample to be tested within or on the sample support element coupled to the channel between the mixing and detection zones, wherein the inlet and the coupling channel are configured to draw the sample to be tested into the mixing zone; the test device including a movement unit operable to effect movement of the sample to be tested.

25. A combination according to claim 24, wherein the movement unit is operable to apply a magnetic field to effect movement of the sample to be tested.

26. A method of testing for the presence of a substance in a sample using a sample carrier, comprising:
connecting a sample carrier according to claim 1 to a test device;
obtaining a sample and depositing the sample in the inlet;
operating the test device to sense one or more parameters relating to the contents or characteristics of the sample.

27. A method according to claim 26, further comprising determining a diagnostic condition on the basis of the sensed parameter or parameters.

* * * * *